US008119150B2

(12) United States Patent
Tamarkin et al.

(10) Patent No.: US 8,119,150 B2
(45) Date of Patent: *Feb. 21, 2012

(54) NON-FLAMMABLE INSECTICIDE COMPOSITION AND USES THEREOF

(75) Inventors: Dov Tamarkin, Ness Ziona (IL); Doron Friedman, Karmei Yosef (IL); Meir Eini, Ness Ziona (IL)

(73) Assignee: Foamix Ltd., Rehovot (IL)

( * ) Notice: Subject to any disclaimer, the term of this patent is extended or adjusted under 35 U.S.C. 154(b) by 1265 days.

This patent is subject to a terminal disclaimer.

(21) Appl. No.: 11/481,596

(22) Filed: Jul. 6, 2006

(65) Prior Publication Data

US 2007/0020304 A1    Jan. 25, 2007

Related U.S. Application Data

(63) Continuation-in-part of application No. 10/911,367, filed on Aug. 4, 2004, application No. 11/481,596, which is a continuation-in-part of application No. 10/532,618, filed as application No. PCT/IB03/05527 on Oct. 24, 2003.

(60) Provisional application No. 60/492,385, filed on Aug. 4, 2003, provisional application No. 60/429,546, filed on Nov. 29, 2002, provisional application No. 60/696,878, filed on Jul. 6, 2005.

(30) Foreign Application Priority Data

Oct. 25, 2002 (IL) ............................. 152486

(51) Int. Cl.
*A01N 25/34* (2006.01)
*A01N 25/00* (2006.01)
(52) U.S. Cl. ........................ 424/403; 424/405
(58) Field of Classification Search .................. None
See application file for complete search history.

(56) References Cited

U.S. PATENT DOCUMENTS

| | | | |
|---|---|---|---|
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,968,628 A | 1/1961 | Reed |
| 3,062,715 A | 11/1962 | Reese |
| 3,067,784 A | 12/1962 | Gorman |
| 3,092,255 A | 6/1963 | Hohman |
| 3,141,821 A | 7/1964 | Compeau |
| 3,142,420 A | 7/1964 | Gawthrop |
| 3,144,386 A | 8/1964 | Brighttenback |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienciewicz |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernaadez |
| 3,346,451 A | 10/1967 | Collins et al. |
| 3,366,494 A | 1/1968 | Bower |
| 3,369,034 A | 2/1968 | Chalmers |
| 3,384,541 A | 5/1968 | Clark et al. |
| 3,395,214 A | 7/1968 | Mummert |
| 3,395,215 A | 7/1968 | Warren |
| 3,401,849 A | 9/1968 | Weber, III |
| 3,419,658 A | 12/1968 | Amsdon |
| 3,527,559 A | 9/1970 | Sliwinski |
| 3,559,890 A | 2/1971 | Brooks et al. |
| 3,561,262 A | 2/1971 | Borocki |
| 3,574,821 A | 4/1971 | Pfirrmann et al. |
| 3,577,518 A | 5/1971 | Shepherd |

(Continued)

FOREIGN PATENT DOCUMENTS

AU            198780257            9/1986

(Continued)

OTHER PUBLICATIONS

Barry, B.W. et al, Comparative bio-availability and activity of proprietary topical corticosteroid preparations: vasoconstrictor assays on thirty-one ointments, British Journal of Dermatology, 93, 563-571, 1975.

Martindale, The extra pharmacopoeia [28th] edition, Eds.: Reynolds, J.E.F. and Prasad, A.B., The Pharmaceutical Press, London, pp. 862-864, 1982.

Wormser et al., Protective effect of povidone-iodine ointment against skin lesions induced by sulphur and nitrogen mustards and by non-mustard vesicants, Arch. Toxicol., 1997, 71, 165-170.

Wormser, Early topical treatment with providone-iodine ointment reduces, and sometimes prevents, skin damage following heat stimulus, Letter to the Editor, Burns 24, pp. 383, 1998.

International Search Report and Written Opinion, International Patent Application No. PCT/IB2006/004026, Foamix, Ltd., Jun. 20, 17 pages.

(Continued)

*Primary Examiner* — Alton Pryor
(74) *Attorney, Agent, or Firm* — Wilmer Cutler Pickering Hale and Dorr LLP

(57) ABSTRACT

The present invention provides a safe and effective insecticide composition suitable for treating a subject infested with a parasitic anthropode or to prevent infestation by an arthropod. The insecticide composition is a foamable composition, including a first insecticide; at least one organic carrier selected from a hydrophobic organic carrier, a polar solvent, an emollient and mixtures thereof, at a concentration of about 2% to about 5%, or about 5% to about 10%; or about 10% to about 20%; or about 20% to about 50% by weight; about 0.1% to about 5% by weight of a surface-active agent; about 0.01% to about 5% by weight of at least one polymeric agent selected from a bioadhesive agent, a gelling agent, a film forming agent and a phase change agent; and (5) a liquefied or compressed gas propellant at a concentration of about 3% to about 25% by weight of the total composition.

38 Claims, No Drawings

U.S. PATENT DOCUMENTS

| | | |
|---|---|---|
| 3,751,562 A | 8/1973 | Nichols |
| 3,770,648 A | 11/1973 | Mackes |
| 3,787,566 A | 1/1974 | Gauvreau |
| 3,819,524 A | 6/1974 | Schubert et al. |
| 3,849,580 A | 11/1974 | Weinstein et al. |
| 3,866,800 A | 2/1975 | Schmitt |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom et al. |
| 4,001,391 A | 1/1977 | Feinstone et al. |
| 4,001,442 A | 1/1977 | Stahlberger et al. |
| 4,019,657 A | 4/1977 | Spitzer et al. |
| 4,100,426 A | 7/1978 | Baranowski et al. |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,160,827 A | 7/1979 | Cho et al. |
| 4,213,979 A | 7/1980 | Levine |
| 4,214,000 A | 7/1980 | Papa |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,310,510 A | 1/1982 | Sherman et al. |
| 4,323,694 A | 4/1982 | Scala, Jr. |
| 4,335,120 A | 6/1982 | Holick et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,439,416 A | 3/1984 | Cordon et al. |
| 4,439,441 A | 3/1984 | Hallesy et al. |
| 4,447,486 A | 5/1984 | Hoppe et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,627,973 A | 12/1986 | Moran et al. |
| 4,628,063 A | 12/1986 | Haines et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,741,855 A | 5/1988 | Grote et al. |
| 4,752,465 A | 6/1988 | Mackles |
| 4,770,634 A | 9/1988 | Pellico |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,906,453 A | 3/1990 | Tsoucalas |
| 4,913,893 A | 4/1990 | Varco et al. |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,970,067 A | 11/1990 | Panandiker et al. |
| 4,975,466 A | 12/1990 | Böttcher et al. |
| 4,981,677 A | 1/1991 | Thau |
| 4,981,679 A | 1/1991 | Briggs et al. |
| 4,981,845 A | 1/1991 | Pereira et al. |
| 4,992,478 A | 2/1991 | Geria |
| 5,002,540 A | 3/1991 | Brodman et al. |
| 5,002,680 A | 3/1991 | Schmidt et al. |
| 5,007,556 A | 4/1991 | Lover |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,279,819 A | 1/1994 | Hayes |
| 5,286,475 A | 2/1994 | Louvet et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,322,683 A | 6/1994 | Mackles et al. |
| 5,326,557 A | 7/1994 | Glover et al. |
| 5,344,051 A | 9/1994 | Brown |
| 5,352,437 A | 10/1994 | Nakagawa et al. |
| 5,369,131 A | 11/1994 | Poli et al. |
| 5,378,451 A | 1/1995 | Gorman et al. |
| 5,380,761 A | 1/1995 | Szabo et al. |
| 5,384,308 A | 1/1995 | Henkin |

| | | | | | | |
|---|---|---|---|---|---|---|
| 5,385,943 | A | 1/1995 | Nazzaro-Porro | 5,866,040 A | 2/1999 | Nakama et al. |
| 5,389,676 | A | 2/1995 | Michaels | 5,869,529 A | 2/1999 | Sintov et al. |
| 5,397,312 | A | 3/1995 | Rademaker et al. | 5,871,720 A | 2/1999 | Gutierrez et al. |
| 5,411,992 | A | 5/1995 | Eini et al. | 5,877,216 A | 3/1999 | Place et al. |
| 5,422,361 | A | 6/1995 | Munayyer et al. | 5,879,469 A | 3/1999 | Avram et al. |
| 5,429,815 | A | 7/1995 | Faryniarz et al. | 5,885,581 A | 3/1999 | Massand |
| 5,435,996 | A | 7/1995 | Glover et al. | 5,889,028 A | 3/1999 | Sandborn et al. |
| 5,447,725 | A | 9/1995 | Damani et al. | 5,889,054 A | 3/1999 | Yu et al. |
| 5,449,520 | A | 9/1995 | Frigerio et al. | 5,891,458 A | 4/1999 | Britton et al. |
| 5,451,404 | A | 9/1995 | Furman | 5,902,574 A | 5/1999 | Stoner et al. |
| 5,482,965 | A | 1/1996 | Rajadhyaksha | 5,902,789 A | 5/1999 | Stoltz |
| 5,491,245 | A | 2/1996 | Gruning et al. | 5,905,092 A | 5/1999 | Osborne et al. |
| 5,500,211 | A | 3/1996 | George et al. | 5,911,981 A | 6/1999 | Dahms et al. |
| 5,508,033 | A | 4/1996 | Briand et al. | 5,912,007 A | 6/1999 | Pan et al. |
| 5,512,555 | A | 4/1996 | Waldstreicher | 5,914,122 A | 6/1999 | Otterbeck et al. |
| 5,514,367 | A | 5/1996 | Lentini et al. | 5,914,310 A | 6/1999 | Li et al. |
| 5,514,369 | A | 5/1996 | Salka et al. | 5,922,331 A | 7/1999 | Mausner |
| 5,520,918 | A | 5/1996 | Smith | 5,948,682 A | 9/1999 | Moloney |
| 5,523,078 | A | 6/1996 | Baylin | 5,951,993 A | 9/1999 | Scholz et al. |
| 5,527,534 | A | 6/1996 | Myhling | 5,952,373 A | 9/1999 | Lanzendorfer et al. |
| 5,527,822 | A | 6/1996 | Scheiner | 5,952,392 A | 9/1999 | Katz et al. |
| 5,529,770 | A | 6/1996 | McKinzie et al. | 5,955,414 A * | 9/1999 | Brown et al. .................. 510/279 |
| 5,531,703 | A | 7/1996 | Skwarek et al. | 5,961,957 A | 10/1999 | McAnalley |
| 5,534,261 | A | 7/1996 | Rodgers et al. | 5,972,310 A | 10/1999 | Sachetto |
| 5,536,743 | A | 7/1996 | Borgman | 5,976,555 A | 11/1999 | Liu et al. |
| 5,540,853 | A | 7/1996 | Trinh et al. | 5,980,904 A | 11/1999 | Leverett et al. |
| 5,545,401 | A | 8/1996 | Shanbrom | 5,993,846 A | 11/1999 | Friedman et al. |
| 5,567,420 | A | 10/1996 | McEleney et al. | 6,006,948 A | 12/1999 | Auer |
| 5,576,016 | A | 11/1996 | Amselem et al. | 6,019,967 A | 2/2000 | Breton et al. |
| 5,578,315 | A | 11/1996 | Chien et al. | 6,024,942 A | 2/2000 | Tanner et al. |
| 5,585,104 | A | 12/1996 | Ha et al. | 6,033,647 A | 3/2000 | Touzan et al. |
| 5,589,157 | A | 12/1996 | Hatfield | 6,039,936 A | 3/2000 | Restle et al. |
| 5,589,515 | A | 12/1996 | Suzuki et al. | 6,042,848 A | 3/2000 | Lawyer et al. |
| 5,603,940 | A | 2/1997 | Candau et al. | 6,045,779 A | 4/2000 | Mueller et al. |
| 5,605,679 | A | 2/1997 | Hansenne et al. | 6,071,536 A | 6/2000 | Suzuki et al. |
| 5,611,463 | A | 3/1997 | Favre | 6,075,056 A | 6/2000 | Quigley, Jr. et al. |
| 5,612,056 | A | 3/1997 | Jenner et al. | 6,080,394 A | 6/2000 | Lin et al. |
| 5,614,171 | A | 3/1997 | Clavenna et al. | 6,087,317 A | 7/2000 | Gee |
| 5,635,469 | A | 6/1997 | Fowler et al. | 6,090,772 A | 7/2000 | Kaiser et al. |
| 5,641,480 | A | 6/1997 | Vermeer | 6,093,408 A | 7/2000 | Hasenoehrl et al. |
| 5,643,600 | A | 7/1997 | Mathur | 6,110,477 A | 8/2000 | Hernandez et al. |
| 5,645,842 | A | 7/1997 | Gruning et al. | 6,113,888 A | 9/2000 | Castro et al. |
| 5,650,554 | A | 7/1997 | Moloney | 6,116,466 A | 9/2000 | Gueret et al. |
| 5,658,749 | A | 8/1997 | Thornton | 6,121,210 A | 9/2000 | Taylor |
| 5,658,956 | A | 8/1997 | Martin et al. | 6,126,920 A | 10/2000 | Jones et al. |
| 5,663,208 | A | 9/1997 | Martin | 6,140,355 A | 10/2000 | Egidio et al. |
| 5,672,634 | A | 9/1997 | Tseng et al. | 6,146,645 A | 11/2000 | Deckers et al. |
| 5,679,324 | A | 10/1997 | Lisboa et al. | 6,146,664 A | 11/2000 | Siddiqui |
| 5,683,710 | A | 11/1997 | Akemi et al. | 6,162,834 A | 12/2000 | Sebillotte-Arnaud et al. |
| 5,695,551 | A | 12/1997 | Buckingham et al. | 6,165,455 A | 12/2000 | Torgerson et al. |
| 5,700,396 | A | 12/1997 | Suzuki et al. | 6,168,576 B1 | 1/2001 | Reynolds |
| 5,716,611 | A | 2/1998 | Oshlack et al. | 6,171,347 B1 | 1/2001 | Kunz et al. |
| 5,719,122 | A | 2/1998 | Chiodini et al. | 6,180,669 B1 | 1/2001 | Tamarkin |
| 5,719,197 | A | 2/1998 | Kanios et al. | 6,183,762 B1 | 2/2001 | Deckers et al. |
| 5,725,872 | A | 3/1998 | Stamm et al. | 6,186,367 B1 | 2/2001 | Harrold |
| 5,730,964 | A | 3/1998 | Waldstreicher | 6,187,290 B1 | 2/2001 | Gilchrist et al. |
| 5,733,558 | A | 3/1998 | Breton et al. | 6,189,810 B1 | 2/2001 | Nerushai et al. |
| 5,733,572 | A | 3/1998 | Unger et al. | 6,204,285 B1 | 3/2001 | Fabiano et al. |
| 5,747,049 | A | 5/1998 | Tominaga | 6,210,656 B1 | 4/2001 | Touzan et al. |
| 5,753,241 | A | 5/1998 | Ribier et al. | 6,210,742 B1 | 4/2001 | Deckers et al. |
| 5,753,245 | A | 5/1998 | Fowler et al. | 6,214,318 B1 | 4/2001 | Osipow et al. |
| 5,759,520 | A | 6/1998 | Sachetto | 6,221,381 B1 | 4/2001 | Shelford et al. |
| 5,759,579 | A | 6/1998 | Singh et al. | 6,224,888 B1 | 5/2001 | Vatter et al. |
| 5,767,104 | A | 6/1998 | Bar-Shalom et al. | 6,231,837 B1 | 5/2001 | Stroud et al. |
| 5,783,202 | A * | 7/1998 | Tomlinson et al. ............ 424/405 | 6,232,315 B1 | 5/2001 | Shafer et al. |
| 5,792,448 | A | 8/1998 | Dubief et al. | 6,251,369 B1 | 6/2001 | Stoltz |
| 5,792,922 | A | 8/1998 | Moloney | 6,258,374 B1 | 7/2001 | Friess et al. |
| 5,804,546 | A | 9/1998 | Hall et al. | 6,271,295 B1 | 8/2001 | Powell et al. |
| 5,817,322 | A | 10/1998 | Xu et al. | 6,274,150 B1 | 8/2001 | Simonnet et al. |
| 5,824,650 | A | 10/1998 | De Lacharriere et al. | 6,287,546 B1 | 9/2001 | Reich et al. |
| 5,833,960 | A | 11/1998 | Gers-Barlag et al. | 6,294,550 B1 | 9/2001 | Place et al. |
| 5,837,270 | A | 11/1998 | Burgess | 6,299,023 B1 | 10/2001 | Arnone |
| 5,840,744 | A | 11/1998 | Borgman | 6,299,900 B1 | 10/2001 | Reed et al. |
| 5,840,771 | A | 11/1998 | Oldham et al. | 6,305,578 B1 | 10/2001 | Hildebrandt et al. |
| 5,843,411 | A | 12/1998 | Hernandez et al. | 6,306,841 B1 | 10/2001 | Place et al. |
| 5,846,983 | A | 12/1998 | Sandborn et al. | 6,308,863 B1 | 10/2001 | Harman |
| 5,849,042 | A | 12/1998 | Lim et al. | 6,319,913 B1 | 11/2001 | Mak et al. |
| 5,856,452 | A | 1/1999 | Moloney et al. | 6,328,950 B1 | 12/2001 | Franzke et al. |
| 5,858,371 | A | 1/1999 | Singh et al. | 6,333,362 B1 | 12/2001 | Lorant |

| | | | | | |
|---|---|---|---|---|---|
| 6,335,022 B1 | 1/2002 | Simonnet et al. | 7,704,518 B2 * | 4/2010 | Tamarkin et al. .............. 424/405 |
| 6,341,717 B2 | 1/2002 | Auer | 7,820,145 B2 * | 10/2010 | Tamarkin et al. ............... 424/45 |
| 6,344,218 B1 | 2/2002 | Dodd et al. | 2001/0006654 A1 | 7/2001 | Cannell et al. |
| 6,358,541 B1 | 3/2002 | Goodman | 2001/0027218 A1 | 10/2001 | Stern et al. |
| 6,372,234 B1 | 4/2002 | Deckers et al. | 2001/0036450 A1 | 11/2001 | Verite et al. |
| 6,375,960 B1 | 4/2002 | Simonnet et al. | 2002/0002151 A1 | 1/2002 | Ono et al. |
| 6,383,471 B1 | 5/2002 | Chen et al. | 2002/0004063 A1 | 1/2002 | Zhang |
| 6,395,258 B1 | 5/2002 | Steer | 2002/0013481 A1 | 1/2002 | Schonrock et al. |
| 6,395,300 B1 | 5/2002 | Straub et al. | 2002/0015721 A1 | 2/2002 | Simonnet et al. |
| 6,403,061 B1 | 6/2002 | Candau et al. | 2002/0032171 A1 | 3/2002 | Chen et al. |
| 6,403,069 B1 | 6/2002 | Chopra et al. | 2002/0035046 A1 | 3/2002 | Lukenbach et al. |
| 6,410,036 B1 | 6/2002 | De Rosa et al. | 2002/0035087 A1 | 3/2002 | Barclay |
| 6,423,323 B2 | 7/2002 | Neubourg | 2002/0035182 A1 | 3/2002 | L'Alloret et al. |
| 6,428,772 B1 | 8/2002 | Singh et al. | 2002/0039591 A1 | 4/2002 | Dahle |
| 6,433,003 B1 | 8/2002 | Bobrove et al. | 2002/0044659 A1 | 4/2002 | Ohta |
| 6,433,024 B1 | 8/2002 | Popp et al. | 2002/0045659 A1 | 4/2002 | Michelet et al. |
| 6,433,033 B1 | 8/2002 | Isobe et al. | 2002/0048798 A1 | 4/2002 | Avery et al. |
| 6,437,006 B1 | 8/2002 | Yoon et al. | 2002/0058010 A1 | 5/2002 | Picard-Lesboueyries et al. |
| 6,440,429 B1 | 8/2002 | Torizuka et al. | 2002/0072544 A1 | 6/2002 | Miller et al. |
| 6,455,076 B1 | 9/2002 | Hahn et al. | 2002/0098215 A1 | 7/2002 | Douin et al. |
| 6,468,989 B1 | 10/2002 | Chang et al. | 2002/0111281 A1 | 8/2002 | Vishnupad |
| 6,479,058 B1 | 11/2002 | McCadden | 2002/0117516 A1 | 8/2002 | Lasserre et al. |
| 6,486,168 B1 | 11/2002 | Skwierczynski et al. | 2002/0134376 A1 | 9/2002 | Castro et al. |
| 6,488,947 B1 | 12/2002 | Bekele | 2002/0143188 A1 | 10/2002 | Garvey et al. |
| 6,511,655 B1 | 1/2003 | Muller et al. | 2002/0182162 A1 | 12/2002 | Shahinpoor et al. |
| 6,514,487 B1 | 2/2003 | Barr | 2002/0198136 A1 | 12/2002 | Mak et al. |
| 6,524,594 B1 | 2/2003 | Santora et al. | 2003/0006193 A1 | 1/2003 | Ikeda et al. |
| 6,531,118 B1 | 3/2003 | Gonzalez et al. | 2003/0031693 A1 | 2/2003 | Breton et al. |
| 6,534,455 B1 * | 3/2003 | Maurin et al. ................ 510/124 | 2003/0053961 A1 | 3/2003 | Eccard |
| 6,536,629 B2 | 3/2003 | van der Heijden | 2003/0078172 A1 | 4/2003 | Guiramand et al. |
| 6,544,530 B1 | 4/2003 | Friedman | 2003/0175232 A1 | 9/2003 | Elliott et al. |
| 6,548,074 B1 | 4/2003 | Mohammadi | 2003/0175315 A1 | 9/2003 | Yoo et al. |
| 6,562,355 B1 | 5/2003 | Renault | 2003/0185839 A1 | 10/2003 | Podolsky |
| 6,566,350 B2 | 5/2003 | Ono et al. | 2003/0206955 A1 | 11/2003 | Sonneville-Aubrun et al. |
| 6,582,679 B2 | 6/2003 | Stein et al. | 2003/0215472 A1 | 11/2003 | Bonda et al. |
| 6,582,710 B2 | 6/2003 | Deckers et al. | 2004/0018228 A1 | 1/2004 | Fischell et al. |
| 6,589,509 B2 | 7/2003 | Keller et al. | 2004/0028752 A1 | 2/2004 | Kamm et al. |
| 6,596,287 B2 | 7/2003 | Deckers et al. | 2004/0038912 A1 | 2/2004 | Michelet et al. |
| 6,599,513 B2 | 7/2003 | Deckers et al. | 2004/0053797 A1 | 3/2004 | Chen et al. |
| 6,620,773 B1 | 9/2003 | Stork et al. | 2004/0058878 A1 | 3/2004 | Walker |
| 6,649,571 B1 | 11/2003 | Morgan | 2004/0063787 A1 | 4/2004 | Villanueva |
| 6,649,574 B2 | 11/2003 | Cardis et al. | 2004/0078896 A1 | 4/2004 | Hellyer et al. |
| 6,672,483 B1 | 1/2004 | Roy | 2004/0105825 A1 | 6/2004 | Henning |
| 6,682,726 B2 | 1/2004 | Marchesi et al. | 2004/0120917 A1 | 6/2004 | Perrier et al. |
| 6,691,898 B2 | 2/2004 | Hurray et al. | 2004/0127554 A1 | 7/2004 | Ghisalberti |
| 6,709,663 B2 | 3/2004 | Espinoza | 2004/0138179 A1 | 7/2004 | Goldstein et al. |
| 6,730,288 B1 | 5/2004 | Abram | 2004/0151671 A1 | 8/2004 | Abram et al. |
| 6,753,000 B2 | 6/2004 | Breton et al. | 2004/0184992 A1 | 9/2004 | Abram |
| 6,753,167 B2 | 6/2004 | Moloney et al. | 2004/0185123 A1 | 9/2004 | Mazzio et al. |
| 6,762,158 B2 | 7/2004 | Lukenbach et al. | 2004/0191196 A1 | 9/2004 | Tamarkin |
| 6,765,001 B2 | 7/2004 | Gans et al. | 2004/0192754 A1 | 9/2004 | Shapira et al. |
| 6,774,114 B2 | 8/2004 | Castiel et al. | 2004/0197276 A1 | 10/2004 | Takase et al. |
| 6,777,591 B1 | 8/2004 | Chaudhary | 2004/0197295 A1 | 10/2004 | Riedel et al. |
| 6,790,435 B1 | 9/2004 | Ma et al. | 2004/0219122 A1 | 11/2004 | Masuda et al. |
| 6,796,973 B1 | 9/2004 | Contente et al. | 2004/0219176 A1 | 11/2004 | Dominguez |
| RE38,623 E | 10/2004 | Hernandez et al. | 2004/0229813 A1 | 11/2004 | DiPiano et al. |
| 6,811,767 B1 | 11/2004 | Bosch et al. | 2004/0234475 A1 | 11/2004 | Lannibois-Drean et al. |
| 6,834,778 B2 | 12/2004 | Jinbo et al. | 2004/0241099 A1 | 12/2004 | Popp et al. |
| 6,843,390 B1 | 1/2005 | Bristor | 2004/0247531 A1 | 12/2004 | Riedel et al. |
| 6,875,438 B2 | 4/2005 | Kraemer et al. | 2004/0253275 A1 | 12/2004 | Eini et al. |
| 6,902,737 B2 | 6/2005 | Quemin et al. | 2004/0258627 A1 | 12/2004 | Riedel et al. |
| 6,946,120 B2 | 9/2005 | Wai-Chiu So et al. | 2004/0265240 A1 | 12/2004 | Tamarkin et al. |
| 6,946,139 B2 | 9/2005 | Henning | 2005/0002976 A1 | 1/2005 | Wu |
| 6,951,654 B2 | 10/2005 | Malcolm et al. | 2005/0013853 A1 | 1/2005 | Gil-Ad et al. |
| 6,955,816 B2 | 10/2005 | Klysz | 2005/0031547 A1 | 2/2005 | Tamarkin et al. |
| 6,956,062 B2 | 10/2005 | Beilfuss et al. | 2005/0042182 A1 | 2/2005 | Arkin |
| 6,958,154 B2 | 10/2005 | Brandt et al. | 2005/0054991 A1 | 3/2005 | Tobyn et al. |
| 6,969,521 B1 | 11/2005 | Gonzalez et al. | 2005/0069566 A1 | 3/2005 | Tamarkin et al. |
| 7,014,844 B2 | 3/2006 | Mahalingam et al. | 2005/0074414 A1 | 4/2005 | Tamarkin et al. |
| 7,029,659 B2 | 4/2006 | Abram et al. | 2005/0075407 A1 | 4/2005 | Tamarkin et al. |
| 7,060,253 B1 | 6/2006 | Mundschenk | 2005/0079139 A1 | 4/2005 | Jacques et al. |
| 7,078,058 B2 | 7/2006 | Jones et al. | 2005/0084551 A1 | 4/2005 | Jensen et al. |
| 7,137,536 B2 | 11/2006 | Walters et al. | 2005/0101936 A1 | 5/2005 | Gonzales et al. |
| 7,225,518 B2 | 6/2007 | Eidenschink et al. | 2005/0106197 A1 | 5/2005 | Blin et al. |
| 7,235,251 B2 | 6/2007 | Hamer et al. | 2005/0123496 A1 | 6/2005 | Shah et al. |
| 7,270,828 B2 | 9/2007 | Masuda et al. | 2005/0186142 A1 | 8/2005 | Tamarkin et al. |
| 7,645,803 B2 * | 1/2010 | Tamarkin et al. ............... 424/43 | 2005/0186147 A1 | 8/2005 | Tamarkin et al. |
| 7,654,415 B2 | 2/2010 | van der Heijden | 2005/0189377 A1 | 9/2005 | Lanzendorfer et al. |
| 7,700,076 B2 * | 4/2010 | Tamarkin et al. ............... 424/47 | 2005/0196414 A1 | 9/2005 | Dake et al. |

| | | |
|---|---|---|
| 2005/0205086 A1 | 9/2005 | Tamarkin et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0255048 A1 | 11/2005 | Hirsh et al. |
| 2005/0266035 A1 | 12/2005 | Healy et al. |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman |
| 2006/0018938 A1 | 1/2006 | Neubourg |
| 2006/0029565 A1 | 2/2006 | Xu et al. |
| 2006/0057168 A1 | 3/2006 | Larm |
| 2006/0088561 A1 | 4/2006 | Eini et al. |
| 2006/0110418 A1 | 5/2006 | Johnson |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0020213 A1 | 1/2007 | Tamarkin |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0134174 A1 | 6/2007 | Irwin et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0175799 A1 | 7/2009 | Tamarkin et al. |
| 2009/0180970 A1 | 7/2009 | Tamarkin et al. |
| 2009/0317338 A1 | 12/2009 | Tamarkin et al. |
| 2010/0221194 A1 | 9/2010 | Loupenok |
| 2011/0002969 A1 | 1/2011 | Serraima et al. |

FOREIGN PATENT DOCUMENTS

| | | |
|---|---|---|
| DE | 1926796 | 11/1965 |
| DE | 4140474 | 6/1993 |
| DE | 10138495 | 2/2003 |
| DE | 102004016710 | 10/2005 |
| EP | 0156507 A1 | 10/1985 |
| EP | 0186453 | 7/1986 |
| EP | 211550 | 2/1987 |
| EP | 0214865 A2 | 3/1987 |
| EP | 0216856 | 4/1987 |
| EP | 0270316 | 6/1988 |
| EP | 297436 | 1/1989 |
| EP | 326196 | 8/1989 |
| EP | 336812 | 10/1989 |
| EP | 0391124 A2 | 10/1990 |
| EP | 0404376 | 12/1990 |
| EP | 414920 | 3/1991 |
| EP | 0484530 A1 | 5/1992 |
| EP | 485299 | 5/1992 |
| EP | 0488089 A1 | 6/1992 |
| EP | 504301 | 9/1992 |
| EP | 0535327 | 4/1993 |
| EP | 0569773 A2 | 11/1993 |
| EP | 0598412 | 11/1993 |
| EP | 0676198 | 10/1995 |
| EP | 0738516 | 10/1996 |
| EP | 0824911 | 2/1998 |
| EP | 829259 | 3/1998 |
| EP | 928608 | 7/1999 |
| EP | 0979654 A1 | 2/2000 |
| EP | 0993827 A1 | 4/2000 |
| EP | 1055425 A2 | 11/2000 |
| EP | 0506197 | 7/2001 |
| EP | 1215258 | 6/2002 |
| EP | 1287813 | 3/2003 |
| EP | 1308169 | 5/2003 |
| EP | 1428521 | 6/2004 |
| EP | 1438946 | 7/2004 |
| EP | 1189579 | 9/2004 |
| EP | 1475381 | 11/2004 |
| EP | 1483001 | 12/2004 |
| EP | 1500385 | 1/2005 |
| EP | 1600185 | 11/2005 |
| EP | 1734927 | 12/2006 |
| EP | 1758547 | 3/2007 |
| EP | 1584324 | 11/2007 |
| EP | 1889609 | 2/2008 |
| FR | 2736824 | 1/1997 |
| FR | 2774595 A | 8/1999 |
| FR | 2840903 | 12/2003 |
| FR | 2860976 | 4/2005 |
| FR | 2915891 | 11/2008 |
| GB | 808104 | 1/1959 |
| GB | 808105 | 1/1959 |
| GB | 922930 | 4/1963 |
| GB | 933486 | 8/1963 |
| GB | 1026831 | 4/1966 |
| GB | 1033299 | 6/1966 |

| | | | | | | |
|---|---|---|---|---|---|---|
| GB | 1081949 | 9/1967 | | WO | WO-9624325 A1 * | 8/1996 |
| GB | 1121358 | 7/1968 | | WO | WO-96/27376 | 9/1996 |
| GB | 1170152 A | 11/1969 | | WO | WO-96/39119 | 12/1996 |
| GB | 1347950 | 2/1974 | | WO | WO-9703638 * | 2/1997 |
| GB | 1376649 | 12/1974 | | WO | WO-9739745 A1 * | 10/1997 |
| GB | 1397285 | 6/1975 | | WO | WO-9817282 | 4/1998 |
| GB | 1408036 | 10/1975 | | WO | WO-98/18472 | 5/1998 |
| GB | 1489672 | 10/1977 | | WO | WO-98/19654 | 5/1998 |
| GB | 2004746 | 4/1979 | | WO | WO-98/21955 | 5/1998 |
| GB | 1561423 | 2/1980 | | WO | WO-98/23291 | 6/1998 |
| GB | 2114580 | 8/1983 | | WO | WO-98/36733 | 8/1998 |
| GB | 2153686 | 8/1985 | | WO | WO-99/08649 | 2/1999 |
| GB | 2172298 | 9/1986 | | WO | WO-99/20250 | 4/1999 |
| GB | 2166651 | 5/1996 | | WO | WO-99/37282 | 7/1999 |
| GB | 2337461 | 11/1999 | | WO | WO-9953923 | 10/1999 |
| GB | 2406791 | 4/2005 | | WO | WO-00/09082 | 2/2000 |
| IL | 0152486 | 5/2003 | | WO | WO-00/15193 | 3/2000 |
| JP | 60001113 | 4/1978 | | WO | WO-0023051 | 4/2000 |
| JP | 55069682 | 5/1980 | | WO | WO-0033825 | 6/2000 |
| JP | 63119420 | 5/1988 | | WO | WO-0038731 | 7/2000 |
| JP | 01100111 | 4/1989 | | WO | WO-00/61076 | 10/2000 |
| JP | 01156906 | 6/1989 | | WO | WO-00/76461 | 12/2000 |
| JP | 2184614 | 7/1990 | | WO | WO-01/08681 | 2/2001 |
| JP | 02184614 A | 7/1990 | | WO | WO-0110961 A1 | 2/2001 |
| JP | 2255890 | 10/1990 | | WO | WO-01/54679 | 8/2001 |
| JP | 04282311 | 10/1992 | | WO | WO-0162209 | 8/2001 |
| JP | 4312521 | 11/1992 | | WO | WO-01/70242 A2 | 9/2001 |
| JP | 5070340 | 3/1993 | | WO | WO-0182880 A2 | 11/2001 |
| JP | 5213734 | 8/1993 | | WO | WO-0185102 A2 | 11/2001 |
| JP | 6100414 | 4/1994 | | WO | WO-0185128 | 11/2001 |
| JP | 6329532 | 11/1994 | | WO | WO-02/00820 | 1/2002 |
| JP | 7215835 | 8/1995 | | WO | WO-0215860 | 2/2002 |
| JP | 2008040899 | 2/1996 | | WO | WO-0215873 | 2/2002 |
| JP | 8119831 | 5/1996 | | WO | WO-02/28435 | 4/2002 |
| JP | 8165218 | 6/1996 | | WO | WO-02/41847 A1 | 5/2002 |
| JP | 8277209 | 10/1996 | | WO | WO-02/43490 | 6/2002 |
| JP | 9099553 | 4/1997 | | WO | WO-02/062324 | 8/2002 |
| JP | 9110636 | 4/1997 | | WO | WO-02078667 | 10/2002 |
| JP | 10114619 | 5/1998 | | WO | WO-02087519 | 11/2002 |
| JP | 3050289 | 9/1998 | | WO | WO-03000223 A1 | 1/2003 |
| JP | 11250543 | 9/1999 | | WO | WO-03002082 | 1/2003 |
| JP | 2000017174 A | 1/2000 | | WO | WO-03/051294 | 6/2003 |
| JP | 2000080017 | 3/2000 | | WO | WO-03/053292 | 7/2003 |
| JP | 2000128734 | 5/2000 | | WO | WO-03055445 A2 | 7/2003 |
| JP | 2000191429 | 7/2000 | | WO | WO-03055454 | 7/2003 |
| JP | 2000239140 | 9/2000 | | WO | WO-03/075851 | 9/2003 |
| JP | 2000351726 | 12/2000 | | WO | WO-03/092641 | 11/2003 |
| JP | 2000354623 | 12/2000 | | WO | WO-2004017962 | 3/2004 |
| JP | 2001002526 | 1/2001 | | WO | WO-2004/037225 | 5/2004 |
| JP | 2001019606 | 1/2001 | | WO | WO-2004037197 | 5/2004 |
| JP | 2001072963 | 3/2001 | | WO | WO-2004/064833 | 8/2004 |
| JP | 2002012513 | 1/2002 | | WO | WO-2004/071479 A1 | 8/2004 |
| JP | 2002047136 | 2/2002 | | WO | WO-2004064769 | 8/2004 |
| JP | 2002302419 | 10/2002 | | WO | WO-2004/078896 | 9/2004 |
| JP | 2003055146 | 2/2003 | | WO | WO-2004078158 | 9/2004 |
| JP | 2004047136 A | 2/2004 | | WO | WO-2004/093895 | 11/2004 |
| JP | 2004250435 | 9/2004 | | WO | WO-2004/112780 | 12/2004 |
| JP | 2005314323 | 11/2005 | | WO | WO-2005/011567 A2 | 2/2005 |
| JP | 2005350378 | 12/2005 | | WO | WO-2005/018530 | 3/2005 |
| JP | 2006008574 | 1/2006 | | WO | WO-2005/018530 A2 | 3/2005 |
| JP | 2007131539 | 5/2007 | | WO | WO-2005/032522 | 4/2005 |
| KR | 143232 | 7/1998 | | WO | WO-2005/044219 | 5/2005 |
| KR | 2001003063 | 1/2001 | | WO | WO-2005/065652 | 7/2005 |
| UA | 66796 | 6/2004 | | WO | WO-2005063224 | 7/2005 |
| WO | WO-8201821 | 6/1982 | | WO | WO-2005/076697 | 8/2005 |
| WO | WO-86/05389 | 9/1986 | | WO | WO-2005/097068 | 10/2005 |
| WO | WO-88/01863 | 3/1988 | | WO | WO-2005/097068 A1 | 10/2005 |
| WO | WO-8801502 * | 3/1988 | | WO | WO-2005102539 A1 | 11/2005 |
| WO | WO-88/08316 | 11/1988 | | WO | WO-2005/117813 | 12/2005 |
| WO | WO-89/06537 | 7/1989 | | WO | WO-2006/003481 A2 | 1/2006 |
| WO | WO-90/05774 | 5/1990 | | WO | WO-2006/010589 | 2/2006 |
| WO | WO-91/11991 | 8/1991 | | WO | WO-2006011046 | 2/2006 |
| WO | WO-92/00077 | 1/1992 | | WO | WO-2006020682 A1 | 2/2006 |
| WO | WO-9205142 A1 | 4/1992 | | WO | WO-2006/031271 | 3/2006 |
| WO | WO-92/11839 | 7/1992 | | WO | WO-2006028339 A1 | 3/2006 |
| WO | WO-9325189 | 12/1993 | | WO | WO-2006045170 A2 | 5/2006 |
| WO | WO-9406440 | 3/1994 | | WO | WO-2006/091229 | 8/2006 |
| WO | WO-96/03115 | 2/1996 | | WO | WO-2006079632 A1 | 8/2006 |
| WO | WO-96/19921 | 7/1996 | | WO | WO-2006081327 | 8/2006 |

| WO | WO-2006/100485 | | 9/2006 |
| WO | WO-2006/120682 | | 11/2006 |
| WO | WO-2006121610 | A2 | 11/2006 |
| WO | WO-2006122158 | | 11/2006 |
| WO | WO-2006/129161 | | 12/2006 |
| WO | WO-2006/131784 | | 12/2006 |
| WO | WO-2007/007208 | | 1/2007 |
| WO | WO-2007/012977 | | 2/2007 |
| WO | WO-2007/023396 | | 3/2007 |
| WO | WO-2007031621 | A2 | 3/2007 |
| WO | WO-2007/039825 | | 4/2007 |
| WO | WO-2007/050543 | | 5/2007 |
| WO | WO-2007/054818 | | 5/2007 |
| WO | WO-2007/072216 | | 6/2007 |
| WO | WO-2007/085902 | | 8/2007 |
| WO | WO-2007085899 | A2 | 8/2007 |
| WO | WO-2007099396 | A2 | 9/2007 |
| WO | WO-2007111962 | A2 | 10/2007 |
| WO | WO-2008/008397 | | 1/2008 |
| WO | WO-2008010963 | | 1/2008 |
| WO | WO-2008/038147 | | 4/2008 |
| WO | WO-2008/075207 | | 6/2008 |
| WO | WO-2008/087148 | | 7/2008 |
| WO | WO-2008110872 | A2 | 9/2008 |
| WO | WO-2009007785 | A2 | 1/2009 |
| WO | WO-2009069006 | A2 | 6/2009 |
| WO | WO-2009072007 | A2 | 6/2009 |
| WO | WO-2009087578 | A2 | 7/2009 |
| WO | WO-2009090495 | A2 | 7/2009 |
| WO | WO-2009090558 | A2 | 7/2009 |
| WO | WO-2009098595 | A2 | 8/2009 |
| WO | WO-2011039637 | | 4/2011 |
| WO | WO-2011039638 | | 4/2011 |

OTHER PUBLICATIONS

Alcohol SDA 40B.http://www.pharmco-prod.com/pages/MSDS/SDA_40B_200.pdf Accessed Dec. 9, 2008, 2 pages.

Ambrose, Ursual et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.

Arisan, http://www.arisankimya.com/kozmetik.htm Accessed Dec. 10, 2008.

Benet, et al., Application of NMR for the Determination of HLB Values of Nonionic Surfactants, Journal of the American Oil Chemists Society, vol. 49, 1972, 499-500.

Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.

Carbowax 1000MSDS; http://www.sciencelab.com/xMSDS-Polyethylene_glycol_1000-9926622. Accessed Dec. 13, 2008, 6 pages.

Cheshire, et al., Disorders of Sweating, www.medscape.com, Semin Neurol 23(4):399-406, 2003.

Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.

D.W.A. Sharp Dictionary of Chemistry, Penguin Books, 1983, 3 pages.

Dalby, "Determination of Drug Solubility in Aerosol Propellants," Pharmaceutical Research, vol. 8, No. 9, 1991, pp. 1206-1209.

Denatonium Benzoate http://www.newdruginfo.com/pharmaceopeia/usp28/v28230/usp28nf23s0_m22790.htm Accessed Dec. 9, 2008.

Emulsifiers with HLB values. http://www.theherbarie.com/files/resources-center/formulating/Emulsifiers_HLB_Values.pdf accessed Aug. 5, 2009 (3 pps).

Ethanol, Accessed http://www.sigmaaldrich.com/catalog/ProductDetail.do?N4=E7023SIAL&N5=SEARCH_CONCAT_PNOBRAND_KEY&F=SPEC Dec. 9, 2008, 2 pages.

European Patent Application No. 06831721, Official Action, Feb. 3, 2009, 9 pages.

Flick, Cosmetic and Toiletry Formulations, vol. 5, 2nd Edition, Copyright 1996.

Fontana, Anthony, J., "Water Activity: Why It Is Important for Food Safety," International Conference on Food Safety, Nov. 16-18, 1998, 9 pages.

Galligan, John et al., "Adhesive Polyurethane Liners for Anterior Restorations," J. Dent. Res., Jul.-Aug. 1968, pp. 629-632.

Gill, A.M, et al., "Adverse Drug Reactions in a Paediatric Intensitve Care Unit," Acta Paediatr 84:438-441, 1995.

Glaser, et al., Hyperhidrosis: A Comprehensive and Practical Approach to Patient Management, Expert Rev. Dermatol. 1(6), 773-775 (2006).

Gschnait, F., et al., "Topical Indomethacin Protects from UVB and UVA Irriadiation," Arch. Dermatol. Res. 276:131-132, 1984.

Hall, Karla, "Diaper Area Hemanglomas: A Unique Set of Concerns," http://members.tripod.com/~Michelle_G/diaper.html, Dec. 1, 2008, 8 pages.

Hashim, et al. "Tinea versicolor and visceral leishmaniasis," Int J Dermatol., Apr. 1994; 33(4), pp. 258-259 (abstract only).

Hepburn, NC., "Cutaneous leishmaniasis," Clin Exp Dermatol, Jul. 2000; 25(5), pp. 363-370 (abstract only).

Hill, Randall M. (Ed.) Silicone Surfactants, Table of Contents and Chapter 7, "Silicone Surfactants: Applicants in the Personal Care Industry," by David T. Floyd, 1999 (30 Pages).

Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.

International Search Report and Written Opinion, International Application No. PCT/IB2006/003628, Foamix Ltd., Dec. 7, 2007, 15 pages.

International Search Report and Written Opinion, International Application No. PCT/US2007/004459, Foamix Ltd., Dec. 9, 2008, 2 pages.

International Search Report for International Application No. PCT/IB2006/003974, Feb. 25, 2008 (3 pages).

Kalkan, et al., The Measurement of Sweat Intensity Using a New Technique, Tr. J. of Medical Sciences 28, 515-517 (1998).

Kathon™ CG (product information sheet by Rohm and Haas, Jun. 2006).

Kinnunen, Contact Dermatitis Sep. 1989; 21(3): 154-8.

Koerber, S., "Humectants and Water Activity," Water Activity News, 2000, ISSN No. 1083-3943.

Licking Vaginal Dryness without a Prescription. Accessed http://www.estronaut.com/a/vag_dryness.htm on Dec. 14, 2008.

Material Safety Data Sheet, Progesterone, Apr. 26, 2006, 5 pages.

Material Safety Data Sheet, Science Lab.com, Polyethylene Glycol 1000, MSDS, Nov. 6, 2008, 6 pages.

Merriam-Webster Online Dictionaary, 2008, "Mousse," Merriam-Webster Online, Dec. 8, 2008 http://www.merriam-webster.com/dictionary/mousse.

Metronidazole. www.usp.org/pdf/EN/veterinary/metronidazole.pdf. accessed Sep. 10, 2009, 4 pages.

Morgan, Timothy M., et al., "Enhanced Skin Permeation of Sex Hormones with Novel Topical Spray Vehicles," Journal of Pharmaceutical Sciences, vol. 87, No. 10, Oct. 1998, pagse 1213-1218.

OM Cinnamate. http://www.makingcosmetics.com/sunscreens/OM-Cinnamate-p102.html accessed Sep. 26, 2009.

Pendergrass, "The shape and dimensions of the human vagina as seen in three-dimensional vinyl polysiloxane casts," Gynecol Obstet. Invest. 1996:42(3):178-82 (abstract).

Progesterone MSDS. http://www.usp.org.pdf.EN/referenceStandards/msds/1568007.pdf on Dec. 14, 2002, 5 pages.

Savin, et al., "Tinea versicolor treated with terbinafine 1% solution," Int J. Dermatol, Nov. 1999; 38(11), pp. 863-865.

Schmidt A., "Malassezia furfur: a fungus belonging to the physiological skin flora and its relevance in skin disorders," Curtis., Jan. 1997; 59(1), pp. 21-24 (abstract).

Scott as Published in Pharmaceutical Dosage Forms; Disperse Systems, vol. 3, Copyright 1998.

Shear, et al., "Pharmacoeconomic analysis of topical treatments for tinea infections," Pharmacoeconomics. Mar. 1995; 7(3); pp. 251-267 (abstract only).

Sigma Aldrich, "HLB-Numbers In Lithography Nanopatterning," http://www.sigmaaldrich.com/materials-science/micro-and-nanoelectronics/lithography-nanopatterning/hlb-numbers.html, accessed: Feb. 2, 2009, pp. 1-3.

Sigma-Aldrich, Material Safety Data Sheet, Hydroxyethyl Cellulose, Mar. 3, 2004, 5 pages.

Skin Biology, CP Serum—Copper-Peptide Serum for Skin Regeneration and Reducing Wrinkles, Skin Biology, http://web.archive.org/web/20030810230608/http://www.skinbio.com/cpserum.html, Dec. 1, 2008, 21 pages.

Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only).

Tan et al., "Effect of Carbopol and Polyvinylpyrrolidone on the Mechanical, Rheological, and Release Properties of Bioadhesive Polyethylene Glycol Gels," AAPS PharmSciTech, 2000; 1 (3) article 24 (2000), 10 pages.

Torres-Rodriguez, JM., "New topical antifungal drugs," Arch Med Res. 1993 Winter; 24(4), pp. 371-375 (abstract).

Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008.

"HLB Systems", http://pharmcal.tripod.com/ch17.htm, Accessed Sep. 17, 2010, pp. 1-3.

Adachi, Shuji. "Storage and Oxidative Stability of O/W/ Nano-emulsions." *Foods Food Ingredients. J. Jpn*. vol. 209, No. 11. 2004. 1 page.

Anton, N. et al. "Water-in-Oil Nano-Emulsion Formation by the phase inversion Temperature Method: A Novel and General Concept, a New Template for Nanoencapsulation." University of Angers. Paris, France. No Date Listed. 2 pages.

Arct, et al., "Common Cosmetic Hydrophilic Ingredients as Penetration Modifiers of Flavonoids", International Journal of Cosmetic Science, 24(6):357-366 (2002)—Abstract, 1 page.

Arisan, http://www.arisankimya.com/kozmetik.htm Accessed Dec. 10, 2008, 8 pages.

Augsburger, Larry L. et al. "Bubble Size Analysis of High Consistency Aerosol Foams and Its Relationship to Foam Rheology. Effects of Container Emptying, Propellent Type, and Time." *Journal of Pharmaceutical Sciences*. vol. 57, No. 4. Apr. 1968. pp. 624-631.

Austria, et al., "Stability of Vitamin C Derivatives in Solution and Topical Formulations", Journal of Pharmaceutical and Biomedical Analysis, 15:795-801 (1997).

Bernstein, et al., Effects of the Immunomodulating Agent R837 on Acute and Latent Herpes Simplex Virus Type 2 Invections, Antimicrobial Agents and Chemotherapy, 33(9):1511-1515 (1989).

Blute, et al., "Phase Behavious of Alkyl Glycerol Ether Surfacants", Tenside Surf. Det., 35(3):206-212 (1998).

Brenes, et al., "Stability of Copigmented Anthocyanins and Asorbics Acid in a Grape Juice Model System", J. Agric Food Chem, 53(1):49-56 (2005)—Abstract, 1 page.

Bronopol. Retrieved online on Jun. 4, 2011. <URL:http://chemicalland21.com/specialtychem/perchem/BRONOPOL.html>. Jul. 17, 2006. 4 pages.

Buck, et al., "Treatment of Vaginal Intraephithelial Neoplasia (Primarily Low Grade) with Imiquimod 5% Cream", Journal of Lower Genetial Tract Disease, 7(3):290-293 (2003).

Bunker, et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (3 pages).

Burton, et al., "Hypertrichosis Due to Minoxidil", British Journal of Dermatology, 101:593-595 (1979).

Campos, et al., "Ascorbic Acid and Its Derivatives in Cosmetic Formulations", Cosmetics and Toiletries, 115(6):59-62 (2000)—Abstract, 1 page.

Carelli, et al., "Effect of Vehicles on Yohimbine Permeation Across Excised Hairless Mouse Skin", Pharm Acta Helv, 73(3):127-134 (1998)—Abstract, 1 page.

Chebil, et al., "Soulbility of Flavonoids in Organic Solvents", J. Chem. Eng. Data, 52(5):1552-1556 (2007)—Abstract, 1 page.

Chevrant-Breton, et al., "Etude du Traitement Capillaire <<Bioscalin>> dans les Alopecies Diffuses de la Femme", Gazette Medicale, 93(17):75-79 (1986).

Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.

Chinnian, et al., "Photostability Profiles of Minoxidil Solutions", PDA J. Pharm Sci Technol., 50(2):94-98 (1996)—Abstract, 1 page.

Chollet, et al., "Development of a Topically Active Imiquimod Formulation", Pharmaceutical Development and Technology, 4(1):35-43 (1999).

Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.

Colloidal Silica. Retrieved online on Jun. 4, 2011. <URL:http://www.grace.com/engineeredmaterials/materialsciences/colloidalsilica/default.aspx>. Copyright 2011. 2 pages.

Croda 2. Croda Cetomacrogol 1000 Product Information Sheet. 2011 (no month given). 1 page.

Croda. Aracel 165 Product Summary. 2011 (no month given). 1 page.

Dawber, et al., "Hypertrichosis in Females Applying Minoxidil Topical Solution and in Normal Controls", JEADV, 17:271-275 (2003).

Dentinger, et al., "Stability of Nifedipine in an Extemporaneously Compounded Oral Solution", American Journal of Health-System Pharmacy, 60(10):1019-1022 (2003)—Abstract, 1 page.

Disorder. In the American Heritage Dictionary of the English Language. Retrieved from http://www.credoreference.com/entry/hmdictenglang/disorder. Accessed Oct. 9, 2010. 1 page.

Draelos, Z. D. "Antiperspirants and the Hyperhidrosis Patients." Dermatologic Therapy. 2001. vol. 14. pp. 220-224.

Edens, et al., "Storage Stability and Safey of Active Vitamin C in a New Dual-Chamber Dispenser", Journal of Applied Cosmetology, 17(4):136-143 (1999)—Abstract, 1 page.

Edirisinghe, et al., "Effect of fatty acids on endothelium-dependent relaxation in the rabbit aorta", Clin Sci (Lond). Aug. 2006; 111(2): 145-51.

Edwards, "Imiquimod in Clinical Practice", J. Am Acad Dermatol., 43(1, Pt 2):S12-S17 (2000)—Abstract, 1 page.

Encyclopedia of Pharmaceutical Technology, Second Edition, vol. 3, Copyright 2002, 4 pages.

English translation of abstract for Japanese Patent Publication No. S4892282 (1992) (1 page).

Esposito, E. et al. "Nanosystems for Skin Hydration: A Comparative Study." *International Journal of Cosmetic Science*. 29. 2007. pp. 39-47.

Farahmand, et al., "Formulation and Evaluation of a Vitamin C Multiple Emulsion", Pharmaceutical Development and Technology, 11(2):255-261 (2006)—Abstract, 1 page.

Final Office Action for U.S. Appl. No. 11/430,437, Tamarkin et al., Dec. 16, 2008, 24 pages.

Gallarate, et al., "On the Stability of Ascorbic Acid in Emulsified Systems for Topical and Cosmetic Use", International Journal of Pharmaceutics, 188:233-241 (1999).

Gelbard et al. "Primary Pediatric Hyperhidrosis: A Review of Current Treatment Options." Pediatric Dermatology. 2008. 25 (6). pp. 591-598.

Gladkikh, "Ascorbic Acid and Methods of Increasing its Stability in Drugs", Translated from Khimiko-Farmatsevticheskii Zhurnal, 4(12):37-42 (1970)—1 page.

Graves, S. et al. "Structure of Concentrated Nanoemulsions." *The Journal of Chemical Physics.*. 122 America Institute of Physics. Published Apr. 1, 2005. 6 pages.

Groveman, et al., "Lack of Efficacy of Polysorbate 60 in the Treatment of Male Pattern Baldness", Arch Intern Med, 145:1454-1458 (1985).

Hakan, et al., "The protective effect of fish oil enema in acetic acid and ethanol induced colitis," The Turkish Journal of Gasroenterology, 2000, vol. 11, No. 2, pp. 155-161, http://www.turkgastro.org/text/php?id=106, accessed Oct. 8, 2009 (8 pages).

Hallstar. Retrieved online on Jun. 4, 2011. <URL:http://www.hallstar.com/pis.php?product=1H022>. 1 page.

Harrison, et al., "Effects of cytokines and R-837, a cytokine inducer, on UV-irradiation augmented recurrent genital herpes in guinea pigs", Antivial Res., 15(4):315-322 (1991).

Harrison, et al., "Modification of Immunological Responses and Clinical Disease During Topical R-837 Treatment of Genital HSV-2 Infection", Antiviral Research, 10:209-224 (1988).

Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.

Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).

Heart Failure, The Merck Manual, 2008 <<http://www.merck.com/mmhe/sec03/ch025/ch025a.html>> 12 pages.

Hepburn, NC., "Cutaneous leishmaniasis," Clin Exp Dermatol, Jul. 2000; 25(5), pp. 363-370 (abstract only) (1 page).

http://ibabydoc.com/online/diseaseeczema.asp., Atopic Dermatitis, Accessed Jan. 30, 2010. 6 pages.

http://web.archive.org/web/20000106225413/http://pharmacy.wilkes.edu/kibbeweb/lab7.html, Characteristics of Surfactants and Emulsions, Jan. 29, 2010, 5 pages.

http://www.agworkshop.com/p3.asp, AG&Co. Essential oil workshop. 1 page. Accessed Jan. 31, 2010.

Hubbe, Martin. Mini-Encyclopedia of Papermaking Wet-End Chemistry: Additives and Ingredients, their Composition, Functions, Strategies for Use. Retrieved online on Jun. 4, 2011. <URL:http://http://www4.ncsu.edu/~hubbe/CSIL.htm>. Feb. 1, 2001. 4 pages.

ICI Americas Inc. "The HLB System: A Time-Saving Guide to Emulsifier Selection." Mar. 1980. pp. 1-22.

Ikuta, et al., "Scanning Electron Microscopic Observation of Oil/Wax/Water/Surfacant System", Journal of SCCJ, 34(4):280-291 (2004)—Abstract, 1 page.

Indomethacin. Retrieved online on Jun. 3, 2011. <URL:http://it03.net/com/oxymatrine/down/1249534834.pdf>. Aug. 15, 2009. 3 pages.

International Search Report and Written Opinion for International Application No. PCT/IB10/02241 mailed Feb. 10, 2011. 9 pages.

International Search Report and Written Opinion for International Application No. PCT/IB10/02613 mailed Mar. 16, 2011. 9 pages.

International Search Report and Written Opinion for International Application No. PCT/IB10/02617 mailed Mar. 15, 2011. 10 pages.

International Search Report from PCT/IB2006/003519, Mailed Dec. 3, 2007.1 page.

International Search Report, International Patent Application No. PCT/IB2007/003463, Foamix, Ltd., Jul. 18, 2008, 6 pages.

International Search Report, International Patent Application No. PCT/IB2007/003759, Foamix Ltd., Jul. 8, 2008 (7 pages).

Invitation to Pay Additional Fees for International Application No. PCT/IB2009/005012 mailed Jul. 27, 2010. 13 pages.

Izquierdo, P. et al. "Formation and Stability of Nano-Emulsions Prepared Using the Phase Inversion Temperature Method." University of Barcelona. Sep. 17, 2001. 3 page.

Kanamoto, et al., "Pharmacokinetics of two rectal dosage forms of ketoprofen in patients after anal surgery," J Pharmacobiodyn., Mar. 1988; 11(3):141-5—Abstract, 1 page.

Kang,et al., "Enhancement of the Stability and Skin Penetration of Vitamin C by Polyphenol", Immune Netw., 4(4):250-254 (2004)—Abstract, 1 page.

Karasu, T.B. et al., "Treatment of Patients with Major Depressive Disorder, Second Edition," pp. 1-78, 2000.

Kim, "Stability of Minoxidil in Aqueous Solution", Yakhak Hoechi, 30(5):228-231 (1986)—Abstract, 2 page.

Kleber, M.D., H.D. et al., "Treatment of Patients with Substance Use Disorders, Second Edition," pp. 1-276, 2006.

Kreuter, J. "Nanoparticles and microparticles for drug and vaccine delivery," J. Anat. (1996) 189, pp. 503-505.

Kumar, J. et ak., "Application of Broad Spectrum Antiseptic Povidone Iodine as Powerful Action: A Review," Journal of Pharmaceutical Science and Technology vol. 1(2), 2009, 48-58.

Kwak et al. "Study of Complete Transparent Nano-Emulsions which Contain Oils." *IFSCC Conference 2003*, Seoul, Korea, Sep. 22-24, 2003. 3 pages.

Lautenschlager, Dr. Hans. "A Closer Look on Natural Agents: Facts and Future Aspects." Kosmetic Konzept. Kosmetische Praxis. 2006 (no month given). vol. 8, pp. 8-10. 3 pages.

Lebwohl et al. "Treament of Psoriasis. Part 1. Topical Therapy and Phototherapy." J. Am. Acad. Dermatol. 45:487-498. Oct. 2001.

Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).

Leung, et al., "Bioadhesive Drug Delivery in Water-Soluble Polymers," American Chemical Society, Chapter 23, 1991, pp. 350-366.

Li, et al., "Solubility Behavior of Imiquimod in Alkanoic Acids", Abstract 3029, Pharmaceutical Research, vol. 14, No. 11 Supplemental (November), p. S475 (1997), 2 pages.

Lippacher, A. et al. "Liquid and Semisolid SLN Dispersions for Topical Application Rheological Characterization." *European Journal of Pharmaceutics and Biopharmaceutics*. 58. 2004. pp. 561-567.

Lupo, "Antioxidants and Vitamins in Cosmetics", Clinics in Dermatology, 19:467-473 (2001).

Merck Manual Home Edition. "Excessive Sweating: Sweating Disorders." Accessed Apr. 14, 2011 at www.merckmanuals.com/home/print/sec18/ch206/ch206c.html. 2 pages.

Merriam Webster Online Dictionary [online] retrieved from http://www.merriam-webster.com/cgi-bin/dictionary?book=dictionary&va=derivative on Jul. 5, 2008; 1 page.

Messenger, et al., "Minoxidil: Mechanisms of Action on Hair Growth", British Journal of Dermatology, 150:186-194 (2004).

Metz, et al., "A Phase I Study of Topical Tempol for the Prevention of Alopecia Induced by Whole Brain Radiotherapy", Clinical Cancer Research, 10:6411-6417 (2004).

Meucci, et al., "Ascorbic Acid Stability in Aqueous Solutions", Acta Vitaminol Enzymol, 7(3-4):147-153 (1985)—Abstract, 1 page.

MMP Inc. International Development and Manufacturing, "Formulating specialities," http://mmpinc.com, 3 pages. Feb. 2, 2010.

Molan, Peter Clark, "World Wide Wounds," Dec. 2001, 13 pages.

No Author Listed. "Opitmization of Nano-Emulsions Production by Microfluidization." *European Food Research and Technology*. vol. 225, No. 5-6. Sep. 2007. Abstract. 1 page.

Office Action for U.S. Appl. No. 11/430,437, Tamarkin et al., May 9, 2008, 27 pages.

Office Action received from the U.S. Patent Office, U.S. Appl. No. 11/430,599, Jul. 28, 2008 (59 pages).

Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).

Pakpayat, et al., "Formulation of Ascorbic Acid Microemulstions with Alkyl Polyglycosides", European Journal of Pharmaceutics and Biopharmaceutics, 72:444-452 (2009).

Paula. http://ww.cosmeticscop.com/cosmetic-ingredient-dictionary/definition/259/c12-15-alkyl-benzoate.aspx. Printed Oct. 24, 2010. 1 page.

PCT Search Report and Written Opinion for International Application No. PCT/IB2010/001126 mailed Apr. 20, 2011, 12 pages.

Prescription Information for Aldara, Mar. 2007 (29 pages).

Prevent. In the American Heritage Dictionary of the English Language. Retrieved from http://www.credoreference.com/entry/hmdictenglang/prevent. Accessed Oct. 9, 2010. 1 page.

Psoriasis, http://www.quickcare.org/skin/causes-of0psoriasis.html. Accessed Sep. 9, 2010—3 pages.

Purcell, Hal C. "Natural Jojoba Oil Versus Dryness and Free Radicals." *Cosmetics and Toiletries Manufacture Worldwide*. 1988. 4 pages.

Raschke, et al., "Topical Activity of Ascorbic Acid: From In Vitro Optimization to In Vivo Efficacy", Skin Pharmacology and Physiology, 17(4):200-206 (2004)—Abstract, 1 page.

Raymond, Iodine as an Aerial Disinfectant, Journal of Hygiene, vol. 44, No. 5 (May 1946), pp. 359-361.

Rieger, et al. "Emulsfier Selection/HLB." Surficants in Cosmetics. 1997 (no month given). 1 page.

Richwald, "Imiquimod", Drugs Today, 35(7):497 (1999)—Abstract, 1 page.
Rosacea, http://clinuvel.com/skin-conditions/common-skin-conditions/rosacea#h0-6-prevention. Accessed Sep. 9, 2010, 5 pages.
Schutze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages).
Seborrheic Dermatitis, http://www.cumc.columbia.edu/student/health/pdf/R-S/Seborrhea%20Dermatitis.pdf. Access Sep. 9, 2010, 2 pages.
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.
Shim, et al., "Transdermal Delivery of Mixnoxidil with Block Copolymer Nanoparticles", J. Control Release, 97(3):477-484 (2004)—Abstract, 1 page.
Silicone. Definition. Retrieved Apr. 19, 2011 from http://www.oxforddictionaries.com/definition/silicone?view=uk. 1 page.
Simovic, S. et al., "The influence of Processing Variables on Performance of O/W Emulsion Gels Based on Polymeric Emulsifier (Pemulen ®TR-2NF)," International Journal of Cosmetic Science, vol. 2(2): abstract only. Dec. 24, 2001, 1 page.
Skin Deep Cosmetics. PPG-40-PEG-60 Lanolin Oil http://www.cosmeticsdatabase.com/ingredient/722972/PPG-40-PEG-60_Lanolin_Oil/?ingred06=722972. Accessed May 19, 2010. 3 pages.
Sonneville-Aubrun, O. et al. "Nanoemulsions: A New Vehicle for Skincare Products." *Advances in Colloid and Interface Science*. 108-109. 2004. pp. 145-149.
Sreenivasa, et al., "Preparation and Evaluation of Minoxidil Gels for Topical Application in Alopecia", Indian Journal of Pharmaceutical Sciences, 68(4):432-436 (2006), 11 pages.
Stehle, et al., "Uptake of Minoxidil from a New Foam Formulation Devoid of Propylene Glycol to Hamster Ear Hair Follicles", Abstract 606, 1 page.
Sugisaka, et al., "The Physiochemical Properties of Imiquimod, The First Imidazoquinoline Immune Response Modifier", Abstract 3030, Pharmaceutical Research, vol. 14, No. 11 Supplemental (November), p. S475 (1997), 2 pages.
Surfactant. Wikipedia—http://en.wikipedia.org/wiki/surfactant. Printed Oct. 24, 2010. 7 pages.
Sweetman, Sean C. Martindale: The Complete Drug Reference. 33$^{rd}$ Edition. London. Pharmaceutical Press. Jun. 21, 2002. pp. 1073 and 1473. 5 pages.

Tadros, Tharwat F. "Surfactants in Nano-Emulsions." *Applied Surfactants: Principles and Applications.* Wiley-VCH Verlag GmbH & Co. Weinheim. ISBN: 3-527-30629-3. 2005. pp. 285-308.
Tanhehco, "Potassium Channel Modulators as Anti-Inflammatory Agents", Expert Opinion on Therapeutic Patents, 11(7):1137-1145 (2001)—Abstract, 3 pages.
Tarumoto, et al., Studies on toxicity of hydrocortisone 17-butyrate 21-propionate-1. Accute toxicity of hydrocortisone 17-butyrate 21-propionate and its analogues in mice, rats and dogs (authors trans), J Toxicol Sci., Jul. 1981; 6 Suppl: 1-16, Abstract, 1 page.
Tata, et al., "Penetration of Minoxidil from Ethanol Propylene Glycol Solutions: Effect of Application Volume on Occlusion", Journal of Pharmaceutical Sciences, 84(6):688-691 (1995).
Tata, et al., "Relative Influence of Ethanol and Propylene Glycol Cosolvents on Deposition of Minoxidil into the Skin", Journal of Pharmaceutical Sciences, 83(10):1508-1510 (1994).
Trofatter, "imiquimod in clinical Practice", European Journal of Dermatology, 8(7 Supp.):17-19 (1998)—Abstract, 1 page.
Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.
Tsai, et al., "Effect of Minoxidil Concentration on the Deposition of Drug and Vehicle into the Skin", International Journal of Pharmaceutics, 96(1-3):111-117 (1993)—Abstract, 1 page.
Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).
Tyring, "Immune-Response Modifiers: A New Paradigm in the Treatment of Human Papillomavirus", Current Therapeutic Research, 61(9):584-596 (2000)—Abstract, 1 page.
Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." *Pharmazie*. 60. 2005. 5 pages.
Veron, et al., "Stability of Minoxidil Topical Formulations", Ciencia Pharmaceutica, 2(6):411-414 (1992), Abstract, 1 page.
Wermuth, C.G. "Similarity in drugs: reflections on analogue design," Drug Discovery Today, vol. 11, Nos. 7/8, Apr. 2006, pp. 348-354.
Williams, et al., "Scale-up of an Oil/Water Cream Containing 40% Diethylene Glycol Monoethyl Ether", Drug Development and Industrial Pharmacy, 26(1):71-77 (2000).

* cited by examiner

NON-FLAMMABLE INSECTICIDE COMPOSITION AND USES THEREOF

CROSS REFERENCE TO RELATED APPLICATIONS

This application is a continuation-in-part application of co-pending U.S. patent application Ser. No. 10/532,618 filed on Apr. 25, 2005 which is a 371 application of International Patent Application No. IB03/005527, designating the United States and filed on Oct. 24, 2003, which claims the benefit of priority under 35 U.S.C. §119(e) to U.S. Patent Application Ser. No. 60/429,546, filed on Nov. 29, 2002, both entitled "Cosmetic and Pharmaceutical Foam," and which claims the benefit of priority under 35 USC §119(a) to Israeli Patent Application No. 152486, filed Oct. 25, 2002, all of which are hereby incorporated in their entirety by reference.

This application is a continuation-in-part application of co-pending U.S. patent application Ser. No. 10/911,367, filed on Aug. 4, 2004, which claims the benefit of priority under 35 U.S.C. §119(e) to U.S. Patent Application Ser. No. 60/492,385, filed on Aug. 4, 2003, both entitled "Foam Carrier Containing Amphiphilic Copolymer Gelling Agent" and both hereby incorporated in their entirety by reference.

This application claims the benefit of priority under 35 U.S.C. §119(e) to U.S. Patent Application Ser. No. 60/696,878, filed on Jul. 6, 2005, entitled "Non-Flammable Insecticide Composition and Uses Thereof," which is hereby incorporated in its entirety by reference.

BACKGROUND OF THE INVENTION

This invention relates to foamed insecticide compositions.

An insecticide is a compound used to kill or prevent the growth of parasite arthropods, such as insects and/or arachnids and/or crustacean; or a compound used to repel or prevent infestation by parasite arthropods, such as insects and/or arachnids and/or crustacean. Common infestations in humans include lice and scabies.

Infestation with lice is referred to as pediculosis. Lice are ectoparasites that live on the body. The 3 types of lice that parasitize humans are *Pediculus humanus capitis* (head louse), *Pediculus humanus corporis* (body louse), and *Pthirus pubis* (pubic louse).

Every year, between six and 12 million people in the United States, primarily children three to 10 years of age, are infested with head lice. Girls are at greater risk because they have more frequent head-to-head contact. Head lice affect people across the socioeconomic spectrum.

Scabies is an infestation of the skin with the microscopic mite *Sarcoptes scabei*. Infestation is common, found worldwide, and affects people of all races and social classes. Scabies spreads rapidly under crowded conditions where there is frequent skin-to-skin contact between people, such as in hospitals, institutions, child-care facilities, and nursing homes.

Occasionally, a skin infection develops following a bite. Scratching as a result of insect bites can damage the skin and allow bacteria to get in. Infection causes redness and tenderness around the bite, which may gradually spread, and sometimes can become serious.

Resistance of insects to pesticides is commonly known. For example, resistance of lice to 1 percent permethrin has been reported in the US and elsewhere. There are two broad mechanisms by which insect pests develop resistance to insecticides. They may produce large amounts of enzymes, such as esterases which either break down the insecticide molecule or bind to it so tightly that it cannot function (a process known as sequestration). The second mechanism involves mutation of the insecticide target site, such as the acetylcholinesterase enzyme in the nervous system. This effectively blocks the action of the insecticide. Both types of mechanism have been studied in various species of insect.

A common way to overcome resistance is to add a secondary active agent, which impedes that resistance mechanism. An example of such secondary active agent is piperony butoxide, which inhibits the ability of insects to degrade insecticides such as pyrethrum. Another approach is to add volatile solvents such as ethanol and propanol to the insecticide formulation.

U.S. Pat. No. 5,783,202 provides a pediculicidal mousse composition containing (a) from about 0.1 to about 10% w/w of a pediculicidal agent, preferably, pyrethrin, and, optionally from about 0.5 to about 15% w/w of a synergizer therefor, such as piperonyl butoxide, (b) about 70 to about 97% w/w of a foaming agent, which is preferably a quick breaking alcoholic foaming agent; and (c) from about 3 to about 20% w/w of an aerosol propellant.

A pediculocide mousse, which contains the active ingredients piperonyl butoxide (4%) and pyrethrum (0.33%) and the inactive ingredients cetearyl alcohol, isobutane, PEG-20 stearate, propane, propylene glycol, purified water, quaternium-52, SD Alcohol 3-C (26.5% w/w) is commercially available under the name "RID Lice Killing Mousse" (Bayer Corporation). However, this product possesses at least four disadvantages: (1) Irritability: due to the high alcohol content, the incidence of skin and eye irritation is high; (2) "Quick breaking" property: the foam is thermo-sensitive and breaks down rapidly at body temperature so that is cannot easily bespread manually throughout the scalp area; (3) Skin drying; and (4) Inflammability: 26.3% alcohol renders the foam inflammable. A test according to European Standard prEN 14851, titled "Aerosol containers—Aerosol foam flammability test" reveals that this product is inflammable.

Thus, the development of new formulations of permethrin, which will overcome these and other disadvantages, is warranted.

Furthermore, an easy to use product that addresses the frequent skin and eye irritation associated with pediculocide shampoo, cream rinses and lotions is highly desirable.

SUMMARY OF THE INVENTION

The present invention provides a safe and effective insecticide composition. In one aspect, the composition of the present invention is suitable for treating a subject infested with a parasite or preventing infestation by a parasite. In some embodiments, the parasite is an arthropod.

In one or more embodiments, the insecticide composition is a foamable composition, including:

(1) a first insecticide;

(2) at least one organic carrier selected from a hydrophobic organic carrier, a polar solvent, an emollient and mixtures thereof, at a concentration of about 2% to about 5%, or about 5% to about 10%; or about 10% to about 20%; or about 20% to about 50% by weight;

(3) a surface-active agent;

(4) about 0.01% to about 5% by weight of at least one polymeric agent selected from a bioadhesive agent, a gelling agent, a film forming agent and a phase change agent; and (5) a liquefied or compressed gas propellant at a concentration of about 3% to about 25% by weight of the total composition.

In another aspect of the present invention, an insecticide composition includes:
(i) a first insecticide;
(ii) an organic carrier, at a concentration of about 5% to about 50%, said organic carrier containing at least one member selected from the group of (1) a second insecticide comprising a plant-derived oil having the ability to kill or prevent the growth of parasite arthropods or to repel or prevent infestation by parasite arthropods, and (2) a potent solvent; and
(iii) a surface-active agent.

In a further embodiment, the insecticide composition contains both (1) a second insecticide, for example, a plant-derived oil having the ability to kill or prevent the growth of parasite arthropods or to repel or prevent infestation by parasite arthropods, and (2) a potent solvent.

In further embodiments, the insecticide is an emulsion, for example, an oil-in-water emulsion.

In still other embodiments, a therapeutic kit provides a safe and effective dosage of an insecticide. The kit includes an aerosol packaging assembly including a container accommodating a pressurized product, and an outlet capable of releasing the pressurized product as a foam. The pressurized product is any of the foamable compositions described herein.

Water and optional ingredients are added to complete the total mass to 100%. All % values are provided on a weight (w/w) basis. Upon release from an aerosol container, the foamable composition forms an expanded foam suitable for topical administration.

DETAILED DESCRIPTION OF THE INVENTION

The foamable insecticide composition is contained in an aerosol container. Upon release from an aerosol container, the foamable composition forms an expanded foam suitable for the treatment of bodies and surfaces.

According to one or more embodiments, the foamable composition is substantially alcohol-free, i.e., free of short chain alcohols. Short chain alcohols, having up to 5 carbon atoms in their carbon chain skeleton and one hydroxyl group, such as ethanol, propanol, isopropanol, butanol, iso-butanol, t-butanol and pentanol, are considered less desirable solvents or polar solvents due to their skin-irritating effect. This disadvantage is particularly meaningful in the case of an insecticide treatment, which is often directed to sensitive and damaged skin and mucosal tissues. Thus, in one or more embodiments, the composition is substantially alcohol-free and includes less than about 5% final concentration of lower alcohols, preferably less than about 2%, more preferably less than about 1%.

Insecticide

In the context of one or more embodiments of the present invention, an insecticide is a compound used to kill or prevent the growth of parasite arthropods, such as insects, arachnids and crustaceans, or a compound used to repel or prevent infestation by these parasite arthropods.

In one or more embodiments, the insecticide is an antibiotic insecticide. Examples of antibiotic insecticides include allosamidin, thuringiensin, spinosad, avermectin insecticides, such as abamectin, doramectin, emamectin, eprinomectin, ivermectin and selamectin, milbemycin insecticides, such as lepimectin, milbemectin, milbemycin oxime and moxidectin, and arsenical insecticides.

In one or more embodiments, the insecticide is a botanical insecticide, such as anabasine, azadirachtin, d-limonene, nicotine, pyrethrins, cinerins, jasmolin, quassia, rotenone, ryania and sabadilla.

In one or more embodiments, the insecticide is a carbamate insecticide. Examples of carbamate insecticides include bendiocarb, carbaryl, benzofuranyl methylcarbamate insecticides, such as benfuracarb, carbofuran, carbosulfan, decarbofuran and furathiocarb, dimethylcarbamate insecticides, such as dimetan, dimetilan, hyquincarb and pirimicarb, oxime carbamate insecticides, such as alanycarb, aldicarb, aldoxycarb, butocarboxim, butoxycarboxim, methomyl, nitrilacarb, oxamyl, tazimcarb, thiocarboxime, thiodicarb and thiofanox, and phenyl methylcarbamate insecticides, such as allyxycarb, aminocarb, bufencarb, butacarb, carbanolate, cloethocarb, dicresyl, dioxacarb, ethiofencarb, fenethacarb, fenobucarb, isoprocarb, methiocarb, metolcarb, mexacarbate, promacyl, promecarb, propoxur, trimethacarb and xylylcarb.

In one or more embodiments, the insecticide is a dinitrophenol insecticides. Examples of dinitrophenol insecticides include dinex, dinoprop and dinosam.

In one or more embodiments, the insecticide is a fluorine insecticide, such as barium hexafluorosilicate, cryolite, sodium fluoride, sodium hexafluorosilicate and sulfluramid.

In one or more embodiments, the insecticide is a formamidine insecticide, such as amitraz, chlordimeform, formetanate and formparanate.

In one or more embodiments, the insecticide is an insect growth regulator. Examples of insect growth regulators include chitin synthesis inhibitors, such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron and triflumuron, juvenile hormone mimics, such as epofenonane, fenoxycarb, hydroprene, kinoprene, methoprene, pyriproxyfen and triprene, juvenile hormones, moulting hormone agonists, such as chromafenozide, halofenozide, methoxyfenozide and tebufenozide, moulting hormones, such as α-ecdysone and ecdysterone, moulting inhibitors, such as diofenolan, precocenes, and dicyclanil.

In one or more embodiments, the insecticide is a nereistoxin analogue insecticide, such as bensultap, cartap, thiocyclam and thiosultap.

In one or more embodiments, the insecticide is a nicotinoid insecticide. Examples of nicotinide insecticides include flonicamid, nitroguanidine insecticides, such as clothianidin, dinotefuran, imidacloprid and thiamethoxam, nitromethylene insecticides, such as nitenpyram and nithiazine, and pyridylmethylamine insecticides, such as acetamiprid, imidacloprid, nitenpyram and thiacloprid.

In one or more embodiments, the insecticide is an organochlorine insecticide. Examples of organochlorine insecticides include bromo-DDT, camphechlor, DDT, lindane, methoxychlor, pentachlorophenol, cyclodiene insecticides, such as aldrin, bromocyclen, chlorbicyclen, chlordane, chlordecone, dieldrin, dilor, endosulfan, endrin, heptachlor, isobenzan, isodrin, kelevan and mirex.

In one or more embodiments, the insecticide is an organophosphorus insecticide. Examples of organophosphorus insecticides include organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naftalofos, phosphamidon, propaphos and tetrachlorvinphos, organothiophosphate insecticides, such as dioxabenzofos, fosmethilan, phenthoate, acethion, amiton, cadusafos, chlorethoxyfos, chlormephos, demephion, demephion, demeton, disulfoton, ethion, ethoprophos, isothioate, malathion, methacrifos, oxydemeton-methyl, oxydeprofos, oxydisulfoton, phorate, sulfotep, terbufos and thiometon, aliphatic amide organothiophosphate insecticides, such as amidithion, cyanthoate, dimethoate, ethoate-methyl, formothion, mecarbam, omethoate, prothoate, sophamide and vamidothion, oxime organothiophosphate insecticides, such as chlorphoxim, phoxim and phoxim-methyl, heterocyclic organothiophosphate insecticides, such as azamethiphos, coumaphos, coumithoate, dioxathion, endothion, menazon, morphothion, phosalone, pyraclofos, pyridaphenthion and quinothion, benzothiopyran organothiophosphate insecticides, such as dithicrofos and thicrofos, benzotriazine organothiophosphate insecticides, such as azinphos-ethyl and azinphos-methyl, isoindole organothiophosphate insecticides, such as dialifos and phosmet, isoxazole organothiophosphate insecticides, such as isoxathion and zolaprofos, pyrazolopyrimidine organothiophosphate insecticides, such as chlorprazophos and pyrazophos; pyridine organothiophosphate insecticides, such as chlorpyrifos and chlorpyrifos-methyl, pyrimidine organothiophosphate insecticides, such as butathiofos, diazinon, etrimfos, lirimfos, pirimiphos-ethyl, pirimiphos-methyl, primidophos, pyrimitate and tebupirimfos, quinoxaline organothiophosphate insecticides, such as quinalphos and quinalphos-methyl, thiadiazole organothiophosphate insecticides, such as athidathion, lythidathion, methidathion and prothidathion, triazole organothiophosphate insecticides, such as isazofos and triazophos, phenyl organothiophosphate insecticides, such as azothoate, bromophos, bromophos-ethyl, carbophenothion, chlorthiophos, cyanophos, cythioate, dicapthon, dichlofenthion, etaphos, famphur, fenchlorphos, fenitrothion, fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos, phosphonate insecticides, such as butonate and trichlorfon, phosphonothioate insecticides such as mecarphon, phenyl ethylphosphonothioate insecticides, such as fonofos and trichloronat, phenyl phenylphosphonothioate insecticides, such as cyanofenphos, EPN and leptophos, phosphoramidate insecticides, such as crufomate, fenamiphos, fosthietan, mephosfolan, phosfolan and pirimetaphos, phosphoramidothioate insecticides, such as acephate, isocarbophos, isofenphos, methamidophos and propetamphos, and phosphorodiamide insecticides, such as dimefox, mazidox, mipafox and schradan.

In one or more embodiments, the insecticide is an oxadiazine insecticide, such as indoxacarb.

In one or more embodiments, the insecticide is a phthalimide insecticide, such as dialifos, phosmet and tetramethrin.

In one or more embodiments, the insecticide is a pyrazole insecticide, such as acetoprole, ethiprole, fipronil, pyrafluprole, pyriprole, tebufenpyrad, tolfenpyrad and vaniliprole.

In one or more embodiments, the insecticide is a pyrethroid insecticide. Examples of pyrethroid insecticides include pyrethroid ester insecticides, such as acrinathrin, allethrin, bioallethrin, barthrin, bifenthrin, bioethanomethrin, cyclethrin, cycloprothrin, cyfluthrin, beta-cyfluthrin, cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin, and pyrethroid ether insecticides, such as etofenprox, flufenprox, halfenprox, protrifenbute and silafluofen.

In one or more embodiments, the insecticide is a pyrimidinamine insecticide, such as flufenerim and pyrimidifen.

In one or more embodiments, the insecticide is a pyrrole insecticide, such as chlorfenapyr.

In one or more embodiments, the insecticide is a tetronic acid insecticide, such as spiromesifen and spirotetramat.

In one or more embodiments, the insecticide is a thiourea insecticide, such as diafenthiuron.

In one or more embodiments, the insecticide is a urea insecticide, such as flucofuron and sulcofuron.

Yet, in additional embodiments, the insecticide is an unclassified insecticide, such as closantel, crotamiton, fenazaflor, fenoxacrim, flubendiamide, hydramethylnon, isoprothiolane, malonoben, metaflumizone, metoxadiazone, nifluridide, pyridaben, pyridalyl, rafoxanide, triarathene and triazamate.

The above listed insecticides, as well as others not listed, are suitable for use in the composition of the present invention. It is preferred to use insecticides that are approved by the FDA or other health authorities for the treatment of animals and humans.

Non-limiting examples of approved insecticides include hexachlorobenzene, carbamate, naturally occurring pyrethroids, permethrin, allethrin, bioalethrin, phenothrin, malathion and piperonyl butoxide. In a preferred embodiment of the present invention the insecticide is selected from the group consisting of hexachlorobenzene, carbamate, naturally occurring pyrethroids, permethrin, allethrin, bioalethrin, phenothrin, malathion and piperonyl butoxide.

In one or more embodiments, the insecticide is a naturally occurring insecticide compound. As used herein, the term "naturally-occurring insecticide" includes all insecticides that are obtained, derived or extracted from plant or vertebrate sources.

In the context of the present invention, an agent that kills or otherwise affects parasites, such as protozoa is also termed an insecticide (for the purpose of this application terminology only). Exemplary antiparasites are mebendazole, thiabendazole, metronidazole, and praziquantel.

Mixtures of these insecticides may also be employed according to the present invention.

The insecticide is included in the composition of the present invention in a concentration that provides a desirable ratio between the efficacy and safety. Typically, insecticides are included in the composition in a concentration between about 0.05% and about 12% by weight, depending on their potency against the parasitic arthropod to be eradicated. In some embodiments, the concentration is between about 0.5% and about 2% by weight; in other embodiment the concentration is between about 2% and about 5% by weight; and in other embodiments the concentration is between about 5% and about 12% by weight.

In one or more embodiments, the insecticide is encapsulated in particles, microparticles, nanoparticles, microcapsules, spheres, microspheres, nanocapsules, nanospheres, liposomes, niosomes, polymer matrix, nanocrystals or microsponges, and may be manufactured according to known methods.

Organic Carrier

The foamable composition of the present invention can be an emulsion, or microemulsion, including an aqueous phase and an organic carrier phase. The organic carrier is selected from a hydrophobic organic carrier (also termed herein "hydrophobic solvent"), an emollient, a solvent, and a mixture thereof.

A "hydrophobic organic carrier" as used herein refers to a material having solubility in distilled water at ambient temperature of less than about 1 gm per 100 mL, more preferable less than about 0.5 gm per 100 mL, and most preferably less than about 0.1 gm per 100 mL. It is liquid at ambient temperature. The identification of a hydrophobic organic carrier or "hydrophobic solvent", as used herein, is not intended to characterize the solubilization capabilities of the solvent for any specific active agent or any other component of the foamable composition. Rather, such information is provided to aid in the identification of materials suitable for use as a hydrophobic carrier in the foamable compositions described herein.

In one or more embodiments, the hydrophobic organic carrier is an oil, such as mineral oil. According to one or more embodiments, the hydrophobic solvent is a liquid oil originating from vegetable, marine or animal sources. Suitable liquid oil includes saturated, unsaturated or polyunsaturated oils. Another class of hydrophobic solvents is the essential oils. Silicone oils also may be used and are desirable due to their known skin protective and occlusive properties.

A further class of organic carriers includes "emollients" that have a softening or soothing effect, especially when applied to body areas, such as the skin and mucosal surfaces. Emollients are not necessarily hydrophobic. Examples of suitable emollients include hexyleneglycol, propylene glycol, isostearic acid derivatives, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, sucrose esters of fatty acids, octyl hydroxystearate and mixtures thereof.

In an embodiment of the present invention, the organic carrier is a polypropylene glycol alkyl ether (PPG alkyl ether). PPG alkyl ethers are liquid, water-insoluble propoxylated fatty alcohols, having the molecular formula of $RO(CH_2CHOCH_3)_n$, wherein "R" is a straight-chained or branched $C_4$ to $C_{22}$ alkyl group; and "n" is in the range between 4 and about 50. They are organic liquids that function as skin-conditioning agent in pharmaceutical and cosmetic formulations. Non-limiting exemplary PPG alkyl ethers include PPG stearyl ethers and PPG butyl ether. Preferred PPG alky ethers according to the present invention include PPG-15 stearyl ether, PPG-2 butyl ether, PPG-9-13 butyl ether and PPG-40 butyl ether.

According to a preferred embodiment, the organic carrier does not contain petrolatum, which is also referred to as "white petrolatum" anord Vaseline". Petrolatum often forms an impermeable occlusive barrier, so that metabolic products and excreta from damaged tissue are not easily removed or drained away. Furthermore, it is difficult for the active drug dissolved in the carrier to pass through the white petrolatum barrier layer into the treated tissue, so the efficacy of the drug is reduced. An additional disadvantage of petroleum jelly-based products relates to the greasy feeling left following their topical application onto the skin, mucosal membranes and wounds causing inconvenience to the user, thereby decreasing treatment compliance.

In one or more embodiments, the organic carrier contains a plant-derived oil, which possesses insecticide properties, i.e., a plant derived oil that has the ability to kill or prevent the growth of parasite arthropods or to repel or prevent infestation by parasite arthropods (herein referred to as a "second hydrophobic insecticide" or "plant derived insecticide").

Examples of plant-derived insecticides include but are not limited to the oils of anise, bergemont, canola, cassia, catnip, cedarwood, citronella, clove, eucalyptus, garlic, ginger, grapefruit, jojova, lavender, lavandin, lemon, lime, orange, peppermint, rosemary, sage, spearmint, star anise, tea tree, tangerine, thyme and white clover.

In one or more embodiments, the "second insecticide" agent is an insect repellent. In one or more embodiment, the insect repellant is a chemical insect repellent, such as diethyl toluamide (DEET). In one or more embodiments, the insect repellent is a naturally-derived Insect repellent.

In one or more embodiments, the insect repellent is repellents that include terpenoid compounds, as described in U.S. Pat. No. 5,411,992, including:

(1) Terpenoid-alcohol or terpene-ols are terpenoids which have at least one hydroxyl group. Examples of terpene-ols include: $C_{10}H_{16}O$ compounds, perillyl alcohol, carveol, myrtenol, and cis-verbenol; $C_{10}H_{18}O$ compounds, myrtanol, iso-pinocampheol, dihydrocarveol, isopulegol, terpineol, terpinen-4-ol, nerol, geraniol, and linalool, and $C_{10}H_{20}O$ compounds, menthol, beta-citronellol, and dihydro-myrcenol.

(2) Terpenoid-esters are terpenoids, which have at least one ester group which is the product of the bonding of the hydroxyl group of a terpene-ol with an aliphatic carboxylic acid that can contain functional groups such as the hydroxyl or amine on the aliphatic chain. Examples of suitable aliphatic carboxylic acids include acetic acid, propionic acid, lactic acid, and various amino acids. Examples of terpenoid-esters include carvyl acetate, carvyl propionate, and menthyl lactate.

(3) Essential oils which contain terpenoids and perfumes which contain terpenoids. Non-limiting examples of essential oils which have high content of terpene-ols and esters include bergamot (62% terpenoids); sage (>50% terpenoids); styrax (>50% terpenoids); peppermint (>50% terpenoids); and pine Siberian (75% terpenoids).

Combining a first insecticide and a second insecticide having different mechanisms of action provides an enhanced and conceivably a synergistic effect against the parasitic arthropods.

Potent Solvent

In one or more embodiments, the organic carrier contains at least one solvent having a high solubilization capacity, termed herein a "potent solvent". In the context of the present invention, a potent solvent is a solvent, other than a short chain alcohol or water, that solubilizes the first and/or second insecticide.

In one or more embodiments, the potent solvent is selected from the group consisting of a polyol, propylene glycol, hexylene glycol, butanediol, diethylene glycol, benzyl alcohol, terpenes, di-terpenes, tri-terpenes, limonene, terpene-ol, dioxolane, dimethylformamide, dimethyl solfoxide (DMSO), methyl dodecyl sulfoxide, ethyl oleate, ethyl caprylate, diisopropyl adipate, dimethylacetamide, N-methylpyrrolidone, N-hydroxyethylpyrrolidone, polyvinylpyrrolidone, dimethylacetamide, azone (1-dodecylazacycloheptan-2-one), 2-(n-nonyl)-1,3-dioxolane, isosorbide derivatives, dimethyl isosorbide, glycofurol and ethoxydiglycol (transcutol) and mixtures thereof in any proportion.

Combining a first insecticide and a potent solvent increase penetration of the insecticide to its target site of action and dissolves the cuticle of the arthropodor the outer surface of the nits, thereby providing an enhanced and conceivably a synergistic effect against the parasitic arthropods.

In one or more embodiments, the organic carrier contains both a second insecticide and a potent solvent. The combination of a first insecticide, a second insecticide and a potent solvent in combination provides an exceptionally effective product for the treatment of parasitic arthropods, as demonstrated in the examples herein.

Polymeric Agent

The polymeric agent serves to stabilize the foam composition and to control drug residence in the target organ. Exemplary polymeric agents are classified below in a non-limiting manner. In certain cases, a given polymer can belong to more than one of the classes provided below.

In one or more embodiments, the polymeric agent includes at least one gelling agent. A gelling agent controls the residence of a therapeutic composition in the target site of treatment by increasing the viscosity of the composition, thereby limiting the rate of its clearance from the site. Many gelling agents are known in the art to possess mucoadhesive properties.

The gelling agent can be a natural gelling agent, a synthetic gelling agent and an inorganic gelling agent. Exemplary gelling agents that can be used in accordance with one or more embodiments of the present invention include, for example, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, starch, chemically modified starches and the like, semi-synthetic polymeric materials such as cellulose ethers (e.g. hydroxyethyl cellulose, hydroxypropyl cellulose, methyl cellulose, carboxymethyl cellulose, methylhydroxyethylcellulose, methylhydroxypropylcellulose, hydroxypropylmethyl cellulose, hydroxyethylcarboxymethylcellulose, carboxymethylcellulose and carboxymethylhydroxyethylcellulose), guar gum, hydroxypropyl guar gum, soluble starch, cationic celluloses, cationic guars, and the like, and synthetic polymeric materials, such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like. Mixtures of the above compounds are contemplated.

Further exemplary gelling agents include the acrylic acid/ethyl acrylate copolymers and the carboxyvinyl polymers, which consist essentially of a colloidal water-soluble polyalkenyl polyether crosslinked polymer of acrylic acid crosslinked with a crosslinking agent such as polyallyl sucrose or polyallyl pentaerythritol. Examples include Carbopol® 934, Carbopol® 940, Carbopol® 950, Carbopol® 980, Carbopol® 951 and Carbopol® 981.

The polymeric agent can be an inorganic gelling agent, such as silicone dioxide (fumed silica).

In an embodiment of the present invention, the polymeric agent includes at least one mucoadhesive or bioadhesive agent. Mucoadhesive/bioadhesion has been defined as the attachment of synthetic or biological macromolecules to a biological tissue. Mucoadhesive agents are a class of polymeric biomaterials that exhibit the basic characteristic of a hydrogel, i.e. swell by absorbing water and interacting by means of adhesion with the mucous that covers epithelia. Compositions according to one or more embodiments of the present invention may contain a mucoadhesive macromolecule or polymer in an amount sufficient to confer bioadhesive properties. The bioadhesive macromolecule enhances the delivery of biologically active agents on or through the target surface. The mucoadhesive macromolecule may be selected from acidic synthetic polymers, preferably having at least one acidic group per four repeating or monomeric subunit moieties, such as poly(acrylic)- and/or poly(methacrylic) acid (e.g., Carbopol®, Carbomer®), poly(methylvinyl ether/maleic anhydride) copolymer, and their mixtures and copolymers; acidic synthetically modified natural polymers, such as carboxymethylcellulose (CMC); neutral synthetically modified natural polymers, such as (hydroxypropyl)methylcellulose; basic amine-bearing polymers such as chitosan; acidic polymers obtainable from natural sources, such as alginic acid, hyaluronic acid, pectin, gum tragacanth, and karaya gum; and neutral synthetic polymers, such as polyvinyl alcohol or their mixtures. An additional group of mucoadhesive polymers includes natural and chemically modified cyclodextrin, especially hydroxypropyl-β-cyclodextrin. Such polymers may be present as free acids, bases, or salts, usually in a final concentration of about 0.01% to about 0.5% by weight. Many mucoadhesive agents are known in the art to also possess gelling properties.

In one or more embodiments, the polymeric agent includes at least one film forming polymer. The film forming component may include at least one water-insoluble alkyl cellulose or hydroxyalkyl cellulose. Exemplary alkyl cellulose or hydroxyalkyl cellulose polymers include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or a cross linking agent may be used to modify the polymer's characteristics. For example, esters such as dibutyl or diethyl phthalate, amides such as diethyldiphenyl urea, vegetable oils, fatty acids and alcohols such as oleic and myristyl acid may be used in combination with the cellulose derivative.

In one or more embodiments, the polymeric agent includes at least one phase change polymer, which alters the composition behavior from fluid-like prior to administration to solid-like upon contact with the target mucosal surface. Such phase change results from external stimuli, such as changes in temperature or pH and exposure to specific ions (e.g., $Ca^{2+}$). Non-limiting examples of phase change polymers include poly(N-isopropylamide) and Poloxamer 407®.

The polymeric agent is present in an amount in the range of about 0.01% to about 5.0% by weight of the foam composition. In one or more embodiments, it is typically less than about 1 wt % of the foamable composition.

Surface Active Agent

Surface-active agents (also termed "surfactants") include any agent linking oil and water in the composition, in the form of emulsion. A surfactant's hydrophilic/lipophilic balance (HLB) describes the emulsifier's affinity toward water or oil. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average). The surface active agent according to the present invention has an HLB value, suitable for stabilizing an emulsion comprising the aqueous phase and the organic carrier of the composition.

According to one or more embodiments of the present invention, the surface-active agent has a hydrophilic lipophilic balance (HLB) between about 9 and about 14, which is the required HLB (the HLB required to stabilize an O/W emulsion of a given oil) of most oils and hydrophobic solvents. Thus, in one or more embodiments, the composition contains a single surface active agent having an HLB value between about 9 and 14, and in one or more embodiments, the composition contains more than one surface active agent and the weighted average of their HLB values is between about 9 and about 14. Yet, in other embodiments, when a water in oil emulsion is desirable, the composition contains one or more surface active agents, having an HLB value between about 2 and about 9.

The surface-active agent is selected from anionic, cationic, nonionic, zwitterionic, amphoteric and ampholytic surfactants, as well as mixtures of these surfactants. Such surfactants are well known to those skilled in the therapeutic and cosmetic formulation art. Nonlimiting examples of possible surfactants include polysorbates, such as polyoxyethylene (20) sorbitan monostearate (Tween 60) and poly(oxyethylene) (20) sorbitan monooleate (Tween 80); poly(oxyethylene) (POE) fatty acid esters, such as Myrj 45, Myrj 49, Myrj 52 and Myrj 59; poly(oxyethylene) alkylyl ethers, such as poly(oxyethylene) cetyl ether, poly(oxyethylene) palmityl ether, polyethylene oxide hexadecyl ether, polyethylene glycol cetyl ether, brij 38, brij 52, brij 56 and brij W1; sucrose esters, partial esters of sorbitol and its anhydrides, such as sorbitan monolaurate and sorbitan monolaurate; mono or diglycerides, isoceteth-20, sodium methyl cocoyl taurate, sodium methyl oleoyl taurate, sodium lauryl sulfate, triethanolamine lauryl sulfate and betaines.

In one or more embodiments of the present invention, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. We have surprisingly found that non-ionic surfactants alone provide foams of excellent quality, i.e. a score of "E" according to the grading scale discussed herein below.

In one or more embodiments, the surface active agent includes a mixture of at least one non-ionic surfactant and at least one ionic surfactant in a ratio in the range of about 100:1 to 6:1. In one or more embodiments, the non-ionic to ionic surfactant ratio is greater than about 6:1, or greater than about 8:1; or greater than about 14:1, or greater than about 16:1, or greater than about 20:1.

In one or more embodiments of the present invention, a combination of a non-ionic surfactant and an ionic surfactant (such as sodium lauryl sulphate and cocamidopropylbetaine) is employed, at a ratio of between 1:1 and 20:1, or at a ratio of 4:1 to 10:1. The resultant foam has a low specific gravity, e.g., less than 0.1 g/ml.

The stability of the composition is especially pronounced when a combination of at least one non-ionic surfactant having HLB of less than 9 and at least one non-ionic surfactant having HLB of equal or more than 9 is employed. The ratio between the at least one non-ionic surfactant having HLB of less than 9 and the at least one non-ionic surfactant having HLB of equal or more than 9, is between 1:8 and 8:1, or at a ratio of 4:1 to 1:4. The resultant HLB of such a blend of at least two emulsifiers is between about 9 and about 14.

Thus, in an exemplary embodiment, a combination of at least one non-ionic surfactant having HLB of less than 9 and at least one non-ionic surfactant having HLB of equal or more than 9 is employed, at a ratio of between 1:8 and 8:1, or at a ratio of 4:1 to 1:4, wherein the HLB of the combination of emulsifiers is between about 9 and about 14.

In one or more embodiments of the present invention, the surface-active agent includes mono-, di- and tri-esters of sucrose with fatty acids (sucrose esters), prepared from sucrose and esters of fatty acids or by extraction from sucroglycerides. Suitable sucrose esters include those having high monoester content, which have higher HLB values.

The total surface active agent is in the range of about 0.1 to about 5% of the composition, and is occasionally less than about 2% or less than about 1%.

Foam Adjuvant

Optionally, a therapeutically effective foam adjuvant is included in the foamable compositions of the present invention to increase the foaming capacity of surfactants and/or to stabilize the foam. In one or more embodiments of the present invention, the foam adjuvant agent includes fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). Fatty alcohols, derived from beeswax and including a mixture of alcohols, a majority of which has at least 20 carbon atoms in their carbon chain, are especially well suited as foam adjuvant agents. The amount of the fatty alcohol required to support the foam system is inversely related to the length of its carbon chains. Foam adjuvants, as defined herein are also useful in facilitating improved spreadability and absorption of the composition.

In one or more embodiments of the present invention, the foam adjuvant agent includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

In one or more embodiments, a combination of a fatty acid and a fatty ester is employed.

Optionally, the carbon atom chain of the fatty alcohol or the fatty acid may be saturated or unsaturated, branched or unbranched, or hydroxylated or unhydroxylated. The fatty alcohol or the fatty acid may have at least one double bond. A further class of foam adjuvant agent includes a branched fatty alcohol or fatty acid. The carbon chain of the fatty acid or fatty alcohol also can be substituted with a hydroxyl group, such as 12-hydroxy stearic acid.

Fatty alcohols and fatty acids useful in one or more compositions of the present invention may possess therapeutic properties. Long chain saturated and mono unsaturated fatty alcohols, e.g., stearyl alcohol, erucyl alcohol, arachidyl alcohol and behenyl alcohol (docosanol) have been reported to possess antiviral, antiinfective, antiproliferative and antiinflammatory properties (see, U.S. Pat. No. 4,874,794). Longer chain fatty alcohols, e.g., tetracosanol, hexacosanol, heptacosanol, octacosanol, triacontanol, etc., are also known for their metabolism modifying properties and tissue energizing properties. Long chain fatty acids have also been reported to possess anti-infective characteristics.

Additional Therapeutic Agent

Several conditions involve a combination of etiological factors, some of which are related to the arthropod or another parasite infestation (that can be affected by an insecticide); and other etiological factors that require an additional therapeutic modality. For example, pediculosis may involve lice infection as well as secondary infection or inflammation, and therefore combined treatment with an insecticide and an anti-inflammatory agent or an antibiotic agent would be beneficial. Likewise, rosacea, which involves a parasite infection, inflammation and telangiectasia, can benefit from treatment with a combination of metronidazole and an additional therapeutic agent, selected from the group consisting of an anti-inflammatory agent, an immunomodulator, an anti-pruritic agent and a vasoconstrictor. Hence, in many cases, the inclusion of an additional therapeutic agent in the composition of the present invention, contributes to the clinical activity of the insecticide. Thus, in one or more embodiments, the composition further includes at least one additional therapeutic agent, in a therapeutically effective concentration.

In one or more embodiments, the at least one additional therapeutic agent is selected from the group consisting of a steroidal antiinflammatory agent, a nonsteroidal anti-inflammatory drug, an immunosuppressive agent, an immunomodulator, an immunoregulating agent, a hormonal agent, an antibiotic agent, an antifungal agent, an antiviral agent, an antiparasitic agent, a vasoactive agent, a vasoconstrictor, a vasodilator, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, an insecticide, an antiproliferative agent, an anticancer agent, a photodynamic therapy agent, an anti-wrinkle agent, a radical scavenger, a metal oxide (e.g., titanium dioxide, zinc oxide, zirconium oxide, iron oxide), silicone oxide, an anti wrinkle agent, a skin whitening agent, a skin protective agent, a masking agent, an anti-wart agent, a refatting agent, a lubricating agent and mixtures thereof.

The composition of the present invention may further optionally include a variety of formulation excipients, which are added in order to fine-tune the consistency of the formulation, protect the formulation components from degradation and oxidation and modify their consistency. Such excipients may be selected, for example, from stabilizing agents, antioxidants, humectants, preservatives, colorant and odorant agents and other formulation components, used in the art of formulation.

Propellant

Aerosol propellants are used to generate and administer the foamable composition as a foam. The total composition including propellant, foamable compositions and optional ingredients is referred to as the foamable carrier. The propellant makes up about 3% to about 25 wt % of the foamable carrier. Examples of suitable propellants include volatile hydrocarbons such as butane, propane, isobutane or mixtures thereof, chloro-fluoro carbons (CMCs) non-ozone-depleting and fluorocarbon propellants, such as 1,1,1,2 tetrafluorethane and 1,1,1,2,3,3,3 heptafluoropropane.

Composition and Foam Physical Characteristics and Advantages

A pharmaceutical or cosmetic composition manufactured using the foam carrier according to one or more embodiments of the present invention is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foam composition of the present invention creates a stable emulsion having an acceptable shelf-life of at least one year, or at least two years at ambient temperature. Plant-derived oils, potent solvents and hydrocarbon propellants, which are a mixture of low molecular weight hydrocarbons, tend to impair the stability of emulsions. It has been observed, however, that emulsion compositions according to the present invention are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam.

The foam of the present invention has several advantages, when compared with hydroalcoholic foam compositions, such as described in U.S. Pat. No. 5,783,202:

(1) Breakability. The foam of the present invention is thermally stable. Unlike hydroalcoholic foam compositions the foam of the present invention is not "quick breaking", i.e., it does not readily collapse upon exposure to body temperature environment. Sheer-force breakability of the foam is clearly advantageous over thermally-induced breakability, since it allows comfortable application and well directed administration to the target area.

(2) Irritability. The insecticide composition of the present invention are non-irritant, as revealed in clinical trials, unlike the high incidence of skin and eye irritation caused by the hydroalcoholic foam.

(3) Skin drying. Alcohol is known to dry the skin and impair the integrity of the skin barrier. By contrast, the insecticide composition of the present invention is an emulsion, which provides skin refatting and skin barrier building effects.

(4) Inflammability. Alcohol renders the foam inflammable. A test according to European Standard prEN 14851, titled "Aerosol containers—Aerosol foam flammability test" revealed that compositions according to the present invention are non-inflammable, while the hydroalcoholic foam was inflammable.

In terms of usability, the foamable composition is most advantageous, as revealed by clinical trials:

(i) Ease of Application.

Due to the nature a foam product, Foamix Permethrin 1% Foam was found easier to use in comparison with other products available in the market.

When foam is released it expands in the hair and reaches every spot where lice can be found. This advantage is particularly meaningful in regards to such difficult to access areas as in the neck and behind the ears.

Using the product with applicator attached to foam container directly onto the scalp under the hair is very convenient.

(ii) The Foam is Drip-Free

The foam is not liquid and therefore is not leaking when applied.

This allows precise application, without the product being spread on clothes or other parts of the body.

Not a single case of contact with eyes was recorded throughout the study. (It should be noted that the issue of contact with eyes is a common problem when treating with shampoo, lotion and spray which usually cause eye irritation and burning.)

(iii) Patients' Response

Throughout the study it was evident that children enjoy being treated with foam and therefore do not resist the therapy.

Another property of the foam is specific gravity, as measured upon release from the aerosol can. Typically, foams have specific gravity of less than 0.12 g/mL or less than 0.05 g/mL.

Fields of Applications

The present invention provides safe and effective insecticide compositions, suitable to treat any surface or body, infested with an parasitic anthropode, or to prevent infestation by an arthropod. In one or more embodiments, the insecticide composition can be used to kill or prevent the growth of parasite arthropods, such as insects and/or arachnids and/or crustacean. In one or more embodiments, the insecticide composition can be used to repel parasite arthropods or prevent infestation by parasite arthropods.

According to one or more embodiments of the present invention, the insecticide composition is intended for administration to an animal or a human subject. In one or more embodiments, the composition is intended to treat the skin, a body surface, a body cavity or a mucosal surface, e.g., the mucosa of the nose, mouth, eye, ear, respiratory system, vagina or rectum.

In other embodiments, the insecticide composition is intended for the treatment of plants, infested by arthropods.

Yet, in additional embodiments, the insecticide composition of bodies or surfaces other than animal, human or botanical subjects.

The insecticide compositions of the present invention are intended for the treatment of infestation by arthropods, including insects, arachnids and crustaceans. Exemplary arthropods to be treated by the insecticide compositions of the present invention are lice and blowfly larvae, bugs, fleas, gnats, ticks mites, chiggers, punkies, copepods, isopods and barnacles.

The insecticide compositions of the present invention are intended for the prevention of an insect-transmitted disease, such as typhus, Lyme disease, trench fever, leishmeniasis, malaria and relapsing fever.

The following examples exemplify the therapeutic compositions and pharmacological compositions and methods described herein. The examples are for the purposes of illustration only and are not intended to be limiting of the invention.

Example 1

This example describes a foamable insecticide composition containing permethrin (1% or 5%), or malathion (0.5%). The following compositions were prepared by blending the listed ingredients.

|  | Foam A % w/w | Foam B % w/w | Foam C % w/w |
| --- | --- | --- | --- |
| Permethrin (first insecticide) | 1.00 | 5.00 |  |
| Malathion (first insecticide) |  |  | 0.50 |
| Mineral oil | 5.60 | 5.60 | 5.60 |
| Isopropyl myristate | 5.60 | 5.60 | 5.60 |
| Glyceryl monostearate | 0.45 | 0.45 | 0.45 |
| Xanthan gum | 0.25 | 0.25 | 0.25 |
| Methocel K100M | 0.25 | 0.25 | 0.25 |
| Polysorbate 80 | 0.85 | 0.85 | 0.85 |
| PEG-40 stearate | 2.50 | 2.50 | 2.50 |
| Sodium lauryl sulphate | 0.40 | 0.40 | 0.40 |
| Preservative | 0.25 | 0.25 | 0.25 |
| TEA | to pH 5.5 | to pH 5.5 | to pH 5.5 |
| Propane/Butane | 8.00 | 8.00 | 8.00 |
| Purified water | to 100.00 | to 100.00 | to 100.00 |

Example 2

This example describes a foamable insecticide composition containing permethrin (1%), malathion (0.5%) or pyrethrum extract (0.33%)+piperonyl butoxide (4%), as "first insecticide" and diisopropyl adipate and dimethyl isosorbide as potent solvents.

|  | Foam D % w/w | Foam E % w/w | Foam F % w/w |
| --- | --- | --- | --- |
| Permethrin (first insecticide) | 1.00 |  |  |
| Malathion (first insecticide) |  | 0.50 |  |
| Pyrethrum extract (first insecticide) |  |  | 0.33 |
| Piperonyl butoxide (first insecticide) |  |  | 4.00 |
| Diisopropyl adipate (potent solvent) | 3.00 | 3.00 | 3.00 |
| Dimethyl isosorbide (potent solvent) | 10.00 | 10.00 | 10.00 |
| Isopropyl myristate | 5.60 | 5.60 | 5.60 |
| Glyceryl monostearate | 0.45 | 0.45 | 0.45 |
| Xanthan gum | 0.25 | 0.25 | 0.25 |
| Methocel K100M | 0.25 | 0.25 | 0.25 |
| Polysorbate 80 | 0.85 | 0.85 | 0.85 |
| PEG-40 stearate | 2.50 | 2.50 | 2.50 |
| Sodium lauryl sulphate | 0.40 | 0.40 | 0.40 |
| Preservative | 0.25 | 0.25 | 0.25 |
| TEA | to pH 5.5 | to pH 5.5 | to pH 5.5 |
| Propane/Butane | 8.00 | 8.00 | 8.00 |
| Purified water | to 100.00 | to 100.00 | to 100.00 |

Notes:
Depending on the severity of the insect infestation and the target site, the concentration of the permethrin can range between 0.1% and 10%.
Depending on the severity of the insect infestation and the target site, the concentration of malathion can range between 0.1% and 5%.
Depending on the severity of the insect infestation and the target site, the concentration of the pyrethroid extract can range between 0.1% and 10%.

Example 3

This example describes a foamable insecticide composition, containing permethrin (1%), as "first insecticide" and star anise oil as "second insecticide."

|  | Foam G % w/w |
| --- | --- |
| Permethrin (first insecticide) | 1.00 |
| Isopropyl myristate (potent solvent) | 5.60 |
| Star anise oil (second insecticide) | 2.00 |
| Glyceryl monostearate | 0.45 |
| Diisopropyl adipate | 3.00 |
| Xanthan gum | 0.25 |
| Methocel K100M | 0.25 |
| Polysorbate 80 | 0.85 |
| PEG-40 stearate | 2.50 |
| Sodium lauryl sulphate | 0.40 |
| Preservative | 0.25 |
| TEA | to pH 5.5 |
| Propane/Butane | 8.00 |
| Purified water | to 100.00 |

Example 4

This example describes a foamable insecticide composition, concurrently containing permethrin (1%), malathion (0.5%) or pyrethrum extract (0.33%)+piperonyl butoxide (4%), as "first insecticide" and star anise oil as "second insecticide", with or without a potent solvent.

|  | Foam H % w/w | Foam I % w/w | Foam J % w/w |
| --- | --- | --- | --- |
| Permethrin (first insecticide) | 1.00 |  |  |
| Malathion (first insecticide) |  | 0.50 |  |
| Pyrethrum extract (first insecticide) |  |  | 0.33 |
| Piperonyl butoxide (first insecticide) |  |  | 4.00 |
| Diisopropyl adipate (potent solvent) | 3.00 | 3.00 | 3.00 |
| Dimethyl isosorbide (potent solvent) | 10.00 | 10.00 | 10.00 |
| Star anise oil (second insecticide) | 2.00 | 2.00 | 2.00 |

-continued

|  | Foam H % w/w | Foam I % w/w | Foam J % w/w |
|---|---|---|---|
| Isopropyl myristate | 5.60 | 5.60 | 5.60 |
| Glyceryl monostearate | 0.45 | 0.45 | 0.45 |
| Xanthan gum | 0.25 | 0.25 | 0.25 |
| Methocel K100M | 0.25 | 0.25 | 0.25 |
| Polysorbate 80 | 0.85 | 0.85 | 0.85 |
| PEG-40 stearate | 2.50 | 2.50 | 2.50 |
| Sodium lauryl sulphate | 0.40 | 0.40 | 0.40 |
| Preservative | 0.25 | 0.25 | 0.25 |
| TEA | to pH 5.5 | to pH 5.5 | to pH 5.5 |
| Propane/Butane | 8.00 | 8.00 | 8.00 |
| Purified water | to 100.00 | to 100.00 | to 100.00 |

Example 5

This example describes an insecticide composition concurrently containing permethrin (1%), or malathion (0.5%), as "first insecticide"; star anise oil as "second insecticide", with or without a potent solvent.

|  | Emulsion I % w/w | Emulsion II % w/w | Emulsion III % w/w | Emulsion IV % w/w |
|---|---|---|---|---|
| Permethrin (first insecticide) | 1.00 | 1.00 | | |
| Malathion (first insecticide) | | | 0.50 | 0.50 |
| Mineral oil | | | | 5.60 |
| Diisopropyl adipate (potent solvent) | 3.00 | 3.00 | | |
| Dimethyl isosorbide (potent solvent) | 10.00 | | 10.00 | |
| Star anise oil (second insecticide) | 2.00 | 2.00 | 2.00 | 2.00 |
| Isopropyl myristate | 5.60 | 5.60 | 5.60 | 5.60 |
| Glyceryl monostearate | 0.45 | 0.45 | 0.45 | 0.45 |
| Xanthan gum | 0.25 | 0.25 | 0.25 | 0.25 |
| Methocel K100M | 0.25 | 0.25 | 0.25 | 0.25 |
| Polysorbate 80 | 0.85 | 0.85 | 0.85 | 0.85 |
| PEG-40 stearate | 2.50 | 2.50 | 2.50 | 2.50 |
| Preservative | 0.25 | 0.25 | 0.25 | 0.25 |
| TEA | to pH 5.5 | to pH 5.5 | to pH 5.5 | to pH 5.5 |
| Purified water | to 100.00 | to 100.00 | to 100.00 | to 100.00 |

Example 6

This example describes non-occlusive insecticide compositions containing permethrin 5%.

| Ingredient | PER 079 % w/w | PER 091 % w/w |
|---|---|---|
| Permethrin | 5.00 | 5.00 |
| Mineral oil heavy | 22.00 | — |
| Isopropyl myristate | 11.00 | — |
| Benzyl alcohol | 1.50 | 1.50 |
| Glyceryl monostearate | 0.50 | 0.50 |
| Ceteareth-20 | 3.30 | 3.30 |
| Stearyl alcohol | 1.10 | 1.10 |
| Purified water, | 56.75 | 89.75 |
| Carboxymethyl cellulose | 0.55 | 0.55 |
| Glycerin | 3.30 | 3.30 |
| Total product: | 100.00 | 100.00 |

Notes:
Propellant was added to the above compositions at a concentration of 8%.
The total amount of hydrophobic carrier is in the range between 20% and 40%.

Example 7

This example describes additional insecticide compositions containing permethrin 5%.

| Ingredient Name | PER5-092 % w/w | PER5-093 % w/w | PER5-094 % w/w |
|---|---|---|---|
| Permethrin | 5.05 | 5.05 | 5.05 |
| PPG 15 stearyl ether | 15.00 | — | 12.00 |
| Isopropyl myristate | 5.00 | 5.00 | 21.00 |
| Benzyl alcohol | 1.50 | 1.50 | 1.50 |
| Glyceryl monostearate | 0.50 | 0.50 | 1.00 |
| Ceteareth-20 | 3.30 | 3.30 | 3.30 |
| Stearyl alcohol | 1.10 | 1.10 | 1.10 |
| Water, purified | 62.70 | 62.70 | 51.20 |
| Carboxymethyl cellulose | 0.55 | 0.55 | 0.55 |
| Glycerin | — | — | 3.30 |
| Total product: | 100.00 | 100.00 | 100.00 |

Example 8

This example describes an open study to assess the efficacy, safety and usability of a 1% permethrin foam containing a first insecticide, a second insecticide and a potent solvent, in the treatment of head lice (pediculosis capitis) in pediatric patients.

Study Objectives:
1. To assess the efficacy and safety of a 1% Permethrin Foam, in the treatment of head lice (pediculosis capitis) in pediatric patients
2. To detect any side effects of the Foamix 1% Permethrin Foam.
3. To assess the usability of the product.

Methodology:
   The study was performed as a single center open study.
   All patients' parents gave written informed consent to participate in the study.
   The test article, Foamix 1% Permethrin Foam, was applied by the investigator, using an average quantity of 20 gram per patient, according to hair type (length, thickness, curliness etc), on wet or damp hair. The product penetrates under hair via applicator connected to foam container. The foam was spread onto hair through gentle rubbing in. The product remained in contact with hair for 10 minutes and then was washed off with water and a regular shampoo. The same procedure was repeated after 10 days.

24 hours after the first treatment, patients were examined for lice visually and by 2-3 minutes combing. Lice and nits found were counted and recorded.

Dermal side effects (itching, pain, irritation, etc), along with any other adverse events were recorded throughout the study period.

Number of Patients: 56

Diagnosis and Main Criteria for Inclusion:

Healthy male and female pediatric patients, 3 and 15 years of age, diagnosed as having pediculosis capitis.

Test Article: Foam H of Example 4.

Dose: About 20 gr.

Mode of Administration:

The treatment was performed by the Investigator or by one of the staff member, under the Investigator's supervision an average quantity of 20 gr. per patient, according to hair type (length, thickness, curliness, etc), on wet or damp hair (after a 2-3 minutes wash).

The product penetrates under hair via applicator connected to foam container, as shown in the picture below.

The foam was spread onto hair through gentle rubbing in. The product remained in contact with hair for 10 minutes and then was washed off with water and a usual shampoo. Treatment was repeated in 10 days.

In order to measure the applied amount of product, the foam container was weighed before and after every use.

Results and Conclusions:

1. Efficacy:

The product is found effective in lice killing in 96.4% of the patients.

The product further eradicated viable nits in 60% of the patients.

2. Safety:

No drug-related adverse effects were recorded.

3. Usability:

A. Ease of Application.

Due to the nature a foam product, Foamix Permethrin 1% Foam was found easier to use in comparison with other products available in the market.

When foam is released it expands in the hair and reaches every spot where lice can be found. This advantage is particularly meaningful in regards to such difficult to access areas as in the neck and behind the ears.

Using the product with applicator attached to foam container directly onto the scalp under the hair is very convenient.

B. The Foam is Drip-Free

The foam is not liquid and therefore is not leaking when applied.

This allows precise application, without the product being spread on clothes or other parts of the body.

Not a single case of contact with eyes was recorded throughout the study. (It should be noted that the issue of contact with eyes is a common problem when treating with shampoo, lotion and spray which usually cause eye irritation and burning.)

C. Patients' Response

Throughout the study it was evident that children enjoy being treated with foam and therefore do not resist the therapy.

In conclusion, the present study provides evidence that Foam H of Example 4 is safe and effective in the treatment of head lice (pediculosis capitis) in pediatric patients.

Example 9

This example describes a single-blind study of the transepidermal water loss effect of PER 079 and PER 091 vehicle formulations from Example 6 in subjects with normal skin in comparison with Petrolatum and No Treatment.

Transepidermal water loss (TEWL) is often used to assess the occlusive effect of a composition. A single-blind study was carried out to assess the effect of two principal vehicle formulations on TEWL, in comparison with petrolatum (positive control) and no treatment (negative control). Square areas of the same size, 4 cm2 each were drawn in the forearms. The areas were randomly assigned to a single treatment with one of the preparations (PER 079, PER 091 or petrolatum) and one area remained untreated. 40 mg of each of the preparations were applied. The following table provides the TEWL values prior to treatment (baseline) and 30 minutes afterwards.

|  | PER 079 | | PER 091 | | Petrolatum | | No Treatment | |
|---|---|---|---|---|---|---|---|---|
|  | Mean | SE | Mean | SE | Mean | SE | Mean | SE |
| Baseline | 3.8 | 0.4 | 3.8 | 0.5 | 3.8 | 0.5 | 4.1 | 0.5 |
| 30 min | 3.4 | 0.3 | 3.6 | 0.3 | 1.7 | 0.2 | 3.8 | 0.4 |
| % Change | −10.5% | | −5.3% | | −54.3% | | −7.3% | |

The following conclusions had been recorded in light of the study results:

1. The positive control showed a significant decreased of 54.3% in the TEWL values 30 minutes after application, thus confirming that the experimental system responds to a positive control.
2. The negative control (no-treatment) remains stable with negligible decrease of 7.3% after 30 minutes.
3. Formulations PER 079 and PER 091 showed a similar pattern of TEWL change 30 minutes after treatment, with no significant difference between formulations. There was no significant difference in the TEWL change between formulations PER 079 and PER 091 and the negative control.

Hence, it could be concluded that formulations PER 079 and PER 091 are non-occlusive.

What is claimed is:

1. A foamable insecticide composition, including:
   an emulsion, comprising:
   i. a first insecticide;
   ii. at least one organic carrier selected from the group consisting of a hydrophobic organic carrier, an organic polar solvent, an emollient and mixtures thereof, at a concentration of about 2% to about 50% by weight;
   iii. surface active agent;
   iv. about 0.01% to about 5% by weight of at least one polymeric agent selected from the group consisting of bioadhesive agents, gelling agents, film forming agents and phase change agents;
   v. water; and
   vi. liquefied or compressed gas propellant at a concentration of about 3% to about 25% by weight of the total composition;
   wherein the composition is released as a breakable foam that collapses upon application of shear force; and
   wherein the composition includes less than 5% or about 5% by weight of lower alcohols.

2. The insecticide composition of claim 1, wherein said organic carrier comprises at least one member selected from the group of (1) a second insecticide, and (2) a potent solvent.

3. The insecticide composition of claim 2, wherein said organic carrier comprises about 5% to about 50% by weight of said composition and said surface-active agent about 0.1% to about 5% by weight of said composition.

4. The insecticide composition of claim 1, wherein said organic carrier comprises (1) a plant derived insecticide, and (2) a potent solvent.

5. The composition of claim 1 or 2, wherein the emulsion is selected from the group consisting of an oil-in-water emulsion and a water-in-oil emulsion.

6. The composition of claim 1 or 2, wherein the foamable composition includes less than 2% or about 2% by weight of lower alcohols.

7. The composition of claim 1, further including about 0.1% to about 5% by weight of a therapeutically active foam adjuvant is selected from the group consisting of a fatty alcohol having 15 or more carbons in their carbon chain; a fatty acid having 16 or more carbons in their carbon chain; fatty alcohols derived from beeswax and including a mixture of alcohols, a majority of which has at least 20 carbon atoms in their carbon chain; a fatty alcohol having at least one double bond; a fatty acid having at least one double bond; a branched fatty alcohol; a branched fatty acid; a fatty acid substituted with a hydroxyl group; cetyl alcohol; stearyl alcohol; arachidyl alcohol; behenyl alcohol; 1-triacontanol; hexadecanoic acid; stearic acid; arachidic acid; behenic acid; octacosanoic acid; 12-hydroxy stearic acid and mixtures thereof.

8. The composition of claim 1 or 2, wherein the first insecticide is selected from the group consisting of an antibiotic insecticide, a botanical insecticide, a carbamate insecticide, a dinitrophenol insecticide, a fluorine insecticide, an insect growth regulatora chitin synthesis inhibitor, a juvenile hormone mimics, a moulting hormone agonist, a moulting inhibitor, a nereistoxin analogue insecticide, a nicotinoid insecticide, a pyridylmethylamine insecticide, an organochlorine insecticide, a cyclodiene insecticide, an organophosphorus insecticide, an organophosphate insecticide, an organothiophosphate insecticides, an aliphatic amide organothiophosphate insecticide, an oxime organothiophosphate insecticide, a heterocyclic organothiophosphate insecticide, a benzothiopyran organothiophosphate insecticide, a benzotriazine organothiophosphate insecticide, an isoindole organothiophosphate insecticide, an isoxazole organothiophosphate insecticide, a pyrazolopyrimidine organothiophosphate insecticide, a pyridine organothiophosphate insecticide, a pyrimidine organothiophosphate insecticide, a quinoxaline organothiophosphate insecticide, a thiadiazole organothiophosphate insecticide, a triazole organothiophosphate insecticide, such as isazofos and triazophos; a phenyl organothiophosphate insecticides, a phosphonothioate insecticide, a phenyl ethylphosphonothioate insecticide, a phenyl phenylphosphonothioate insecticide, a phosphoramidate insecticide, a phosphoramidothioate insecticide, a phosphorodiamide insecticide, an oxadiazine insecticide, a phthalimide insecticide, a pyrazole insecticide, a pyrethroid insecticide, a pyrethroid ester insecticide, a pyrethroid ether insecticide, a pyrimidinamine insecticide, a pyrrole insecticide, a tetronic acid insecticide, a thiourea insecticide and a urea insecticide.

9. The composition of claim 8, wherein the first insecticide is selected from the group consisting of allosamidin, thuringiensin, spinosad, avermectin, abamectin, doramectin, emamectin, eprinomectin, ivermectin and selamectin, lepimectin, milbemectin, milbemycin oxime and moxidectin, anabasine, azadirachtin, d-limonene, nicotine, pyrethrins, cinerins, jasmolin, quassia, rotenone, ryania, sabadilla, bendiocarb, carbaryl, benfuracarb, carbofuran, carbosulfan, decarbofuran, furathiocarb, dimetan, dimetilan, hyquincarb, pirimicarb, alanycarb, aldicarb, aldoxycarb, butocarboxim, butoxycarboxim, methomyl, nitrilacarb, oxamyl, tazimcarb, thiocarboxime, thiodicarb, thiofanox, allyxycarb, aminocarb, bufencarb, butacarb, carbanolate, cloethocarb, dicresyl, dioxacarb, ethiofencarb, fenethacarb, fenobucarb, isoprocarb, methiocarb, metolcarb, mexacarbate, promacyl, promecarb, propoxur, trimethacarb, xylylcarb, dinex, dinoprop, dinosam, barium hexafluorosilicate, cryolite, sodium fluoride, sodium hexafluorosilicate, sulfluramid, amitraz, chlordimeform, formetanate, formparanate, bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron, triflumuron, epofenonane, fenoxycarb, hydroprene, kinoprene, methoprene, pyriproxyfen, triprene, chromafenozide, halofenozide, methoxyfenozide, tebufenozide, α-ecdysone, ecdysterone, dicyclanil, bensultap, cartap, thiocyclam, thiosultap, flonicamid, clothianidin, dinotefuran, imidacloprid and thiamethoxam, nitenpyram, nithiazine, acetamiprid, imidacloprid, nitenpyram, thiacloprid, bromo-DDT, camphechlor, DDT, lindane, methoxychlor, pentachlorophenol, aldrin, bromocyclen, chlorbicyclen, chlordane, chlordecone, dieldrin, dilor, endosulfan, endrin, heptachlor, isobenzan, isodrin, kelevan, mirex, bromfenvinfos, chlorfenvinphos, crotoxyphos, dichlorvos, dicrotophos, dimethylvinphos, fospirate, heptenophos, methocrotophos, mevinphos, monocrotophos, naftalofos, phosphamidon, propaphos, tetrachlorvinphos, dioxabenzofos, fosmethilan, phenthoate, acethion, amiton, cadusafos, chlorethoxyfos, chlormephos, demephion, demephion, demeton, disulfoton, ethion, ethoprophos, isothioate, malathion, methacrifos, oxydemeton-methyl, oxydeprofos, oxydisulfoton, phorate, sulfotep, terbufos, thiometon, amidithion, cyanthoate, dimethoate, ethoate-methyl, formothion, mecarbam, omethoate, prothoate, sophamide, vamidothion, chlorphoxim, phoxim and phoxim-methyl, azamethiphos, coumaphos, coumithoate, dioxathion, endothion, menazon, morphothion, phosalone, pyraclofos, pyridaphenthion, quinothion, dithicrofos, thicrofos, azinphos-ethyl, azinphos-methyl, dialifos, phosmet, isoxathion, zolaprofos, chlorprazophos, pyrazophos, chlorpyrifos, chlorpyrifos-methyl, butathiofos, diazinon, etrimfos, lirimfos, pirimiphos-ethyl, pirimiphos-methyl, primidophos, pyrimitate, tebupirimfos, quinalphos, quinalphos-methyl, athidathion, lythidathion, methidathion, prothidathion, isazofos, triazophos, azothoate, bromophos, bromophos-ethyl, carbophenothion, chlorthiophos, cyanophos, cythioate, dicapthon, dichlofenthion, etaphos, famphur, fenchlorphos, fenitrothion, fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3, trifenofos, butonate, trichlorfon, mecarphon, fonofos, trichloronat, cyanofenphos, EPN, leptophos, crufomate, fenamiphos, fosthietan, mephosfolan, phosfolan, pirimetaphos, acephate, isocarbophos, isofenphos, methamidophos, propetamphos, dimefox, mazidox, mipafox, schradan, indoxacarb, dialifos, phosmet, tetramethrin, acetoprole, ethiprole, fipronil, pyrafluprole, pyriprole, tebufenpyrad, tolfenpyrad, vaniliprole, acrinathrin, allethrin, bioallethrin, barthrin, bifenthrin, bioethanomethrin, cyclethrin, cycloprothrin, cyfluthrin, beta-cyfluthrin, cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin, etofenprox, flufenprox, halfenprox, protrifenbute, silafluofen, flufenerim, pyrimidifen, chlorfenapyr, spiromesifen, spirotetramat, diafenthiuron, flucofuron, sulcofuron, closantel, crotamiton, fenazaflor, fenoxacrim, flubendiamide, hydramethylnon, isoprothiolane, malonoben, metaflumizone, metoxadiazone, nifluridide, pyridaben, pyridalyl, rafoxanide, triarathene and triazamate.

10. The composition of claim 1 or 2, wherein the concentration range of the first insecticide is selected from the group of (i) between about 0.005% and about 0.5%; (ii) between about 0.5% and about 2%; (iii) between about 2% and about 5%; and (iv) between about 5% and about 12%.

11. The composition of claim 1, wherein upon release from the container, a shear-sensitive foam, having a density range selected from (1) between about 0.02 gr/mL and about 0.1 gr/mL; and (2) between about 0.02 gr/mL and about 0.1 gr/mL, is produced.

12. The composition of claim 1, wherein the foamable composition further contains at least one additional therapeutic agent selected from the group consisting of an a steroidal antiinflammatory agent, an immunosuppressive agent, an immunomodulator, an immunoregulating agent, a hormonal agent, an antibiotic agent, an antifungal agent, an antiviral agent, an antiparasitic agent, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, benzoyl chloride, calcium hypochlorite, magnesium hypochlorite, an anti-wrinkle agent, a radical scavenger, a metal, silver, a metal oxide, titanium dioxide, zinc oxide, zirconium oxide, iron oxide, silicone oxide, talc, carbon, an anti wrinkle agent, a skin whitening agent, a skin protective agent, a masking agent, an anti-wart agent, a refatting agent, a lubricating agent and mixtures thereof.

13. The composition of claim 1, wherein the concentration of the surface active agent is between about 0.1% and about 5%.

14. The composition of claim 1, wherein the emulsion is a water in oil emulsion and wherein the HLB range of the surface active agent is selected from (1) between about 2 and about 9; and (2) between about 9 and about 14.

15. The composition of claim 2, wherein the second insecticide is selected from the group consisting of:
  i. an oil, selected from anise oil, bergemot oil, canola oil, cassia oil, catnip oil, cedarwood oil, citronella oil, clove oil, eucalyptus oil, garlic oil, ginger oil, grapefruit oil, jojova oil, lavender oil, lavandin oil, lemon oil, lime oil, orange oil, peppermint oil, pine oil, rosemary oil, sage oil, spearmint oil, star anise oil, styrax oil, tea tree oil, tangerine oil, thyme oil and white clover oil;
  ii. an insect repellent;
  iv. diethyl toluamide;
  v. a terpenoid compound; and
  vi. a compound selected from the group consisting of perillyl alcohol, carveol, myrtenol, cis-verbenol, myrtanol, iso-pinocampheol, dihydrocarveol, isopulegol, terpineol, terpinen-4-ol, nerol, geraniol, linalool, menthol, beta-citronellol, and dihydro-myrcenol, an ester of a terpene-ol with an aliphatic carboxylic acid, carvyl acetate and carvyl propionate.

16. The composition of claim 2, wherein the potent solvent is selected from the group consisting of a polyol, propylene glycol, hexylene glycol, butanediol, diethylene glycol, benzyl alcohol, terpenes, di-terpenes, tri-terpenes, limonene, terpene-ol, dioxolane, dimethylformanide, dimethyl solfoxide (DMSO), methyl dodecyl sulfoxide, ethyl oleate, ethyl caprylate, diisopropyl adipate, dimethylacetamide, N-methylpyrrolidone, N-hydroxyethylpyrrolidone, polyvinylpyrrolidone, dimethylacetamide, azone (1-dodecylazacycloheptan-2-one), 2-(n-nonyl)-1,3-dioxolane, isosorbide derivatives, dimethyl isosorbide, glycofurol and ethoxydiglycol (transcutol) and mixtures thereof in any proportion.

17. The composition of claim 1, wherein the composition is housed in a pressurized container.

18. The composition of claim 1, wherein the composition is petrolatum-free.

19. The composition of claim 1, wherein the composition is non-occlusive.

20. The composition of claim 1, wherein the composition includes less than 1% or about 1% by weight of lower alcohols.

21. The composition of claim 1, wherein the insecticide is selected from the group consisting of hexachlorobenzene, carbamate, naturally occurring pyrethroids, permethrin, allethrin, bioalethrin, phenothrin, malathion and piperonyl butoxide.

22. The composition of claim 21, wherein the insecticide is permethrin in a concentration of between 0.1% and 10%.

23. The composition of claim 21, wherein the insecticide is malathion in a concentration of between 0.1% and 5%.

24. The composition of claim 21, wherein the insecticide is metronidazole.

25. The composition of claim 2 or 3, wherein the second insecticide is star anise oil.

26. The composition of claim 2 or 3, wherein the potent solvent is selected from the group consisting of propylene glycol, hexylene glycol, benzyl alcohol, terpene-ol and dimethyl isosorbide.

27. The insecticide composition of claim 1, wherein the surface active agent is non-ionic or a combination of non-ionic and ionic surface active agent, wherein the ratio of non-ionic surface active agent to ionic surface active agent is about 6:1 or greater than 6:1.

28. A foamable insecticide composition, including:
an emulsion comprising:
  i. about 0.5% to about 10% permethrin;
  ii. at least one organic carrier selected from the group consisting of a hydrophobic organic carrier, an organic polar solvent, an emollient and mixtures thereof, at a concentration of about the total amount of hydrophobic carrier is in the range between 20% and 40% by weight;
  iii. about 0.1% to about 5% of a non-ionic surface active agent by weight;
  iv. about 0.01% to about 5% by weight of at least one polymeric agent;
  v. water; and
  vi. liquefied or compressed gas propellant at a concentration of about 3% to about 25% by weight of the total composition, wherein the composition is released as a breakable foam that collapses upon application of shear force; and wherein the composition includes less than 5% or about 5% by weight of lower alcohols.

29. The insecticide composition of claim 28, wherein the surface active agent is non-ionic or a combination of non-ionic and ionic surface active agent, wherein the ratio of non-ionic surface active agent to ionic surface active agent is about 6:1 or greater than 6:1.

30. A method of treating, alleviating or preventing a disorder, wherein the disorder involves a parasitic anthropod infestation as one of its etiological factors, including:
   administering topically to a surface having the disorder, a foamed composition comprising:
   an emulsion comprising:
      i. a first insecticide;
      ii. at least one organic carrier selected from the group consisting of a hydrophobic organic carrier, an organic polar solvent, an emollient and mixtures thereof, at a concentration of about 2% to about 50% by weight;
      iii. surface active agent;
      iv. about 0.01% to about 5% by weight of at least one polymeric agent selected from a bioadhesive agent, a gelling agent, a film forming agent and a phase change agent;
      v. water; and
      vi. liquefied or compressed gas propellant at a concentration of about 3% to about 25% by weight of the total composition,
   wherein the composition is released as a breakable foam that collapses upon application of shear force; and
   wherein the composition includes less than 5% or about 5% by weight of lower alcohols.

31. The method claim 30, wherein said organic carrier comprises at least one member, selected from the group consisting of (1) a second insecticide, and (2) a potent solvent.

32. The method of claim 30, wherein said organic carrier contains both a plant derived insecticide and a potent solvent.

33. The method of claim 30 or 31, wherein the composition includes less than 2% or about 2% by weight of lower alcohols.

34. The method of claim 31, wherein the second insecticide is selected from the group consisting of:
   i. an oil, selected from anise oil, bergemot oil, canola oil, cassia oil, catnip oil, cedarwood oil, citronella oil, clove oil, eucalyptus oil, garlic oil, ginger oil, grapefruit oil, jojova oil, lavender oil, lavandin oil, lemon oil, lime oil, orange oil, peppermint oil, pine oil, rosemary oil, sage oil, spearmint oil, star anise oil, styrax oil, tea tree oil, tangerine oil, thyme oil and white clover oil;
   ii. an insect repellent;
   iv. diethyl toluamide;
   v. a terpenoid compound; and
   vi. a compound selected from the group consisting of perillyl alcohol, carveol, myrtenol, cis-verbenol, myrtanol, iso-pinocampheol, dihydrocarveol, isopulegol, terpineol, terpinen-4-ol, nerol, geraniol, linalool, menthol, beta-citronellol, and dihydro-myrcenol, an ester of a terpene-ol with an aliphatic carboxylic acid, carvyl acetate and carvyl propionate.

35. The method of claim 31, wherein the potent solvent is selected from the group consisting of a polyol, propylene glycol, hexylene glycol, butanediol, diethylene glycol, benzyl alcohol, terpenes, di-terpenes, tri-terpenes, limonene, terpene-ol, dioxolane, dimethylformanide, dimethyl solfoxide (DMSO), methyl dodecyl sulfoxide, ethyl oleate, ethyl caprylate, diisopropyl adipate, dimethylacetamide, N-methylpyrrolidone, N-hydroxyethylpyrrolidone, polyvinylpyrrolidone, dimethylacetamide, azone (1-dodecylazacycloheptan-2-one), 2-(n-nonyl)-1,3-dioxolane, an isosorbide derivative, dimethyl isosorbide, glycofurol and ethoxydiglycol (transcutol) and mixtures thereof in any proportion.

36. The method of claim 30 or 31, wherein the disorder is pediculosis.

37. The method of claim 30 or 31, wherein the first insecticide is selected from the group of include hexachlorobenzene, carbamate, a naturally occurring pyrethroid, permethrin, allethrin, bioalethrin, phenothrin, malathion and piperonyl butoxide.

38. The method of claim 30, wherein the surface active agent is non-ionic or a combination of non-ionic and ionic surface active agent, wherein the ratio of non-ionic surface active agent to ionic surface active agent is about 6:1 or greater than 6:1.

* * * * *